United States Patent
Kaneko et al.

(10) Patent No.: US 6,422,994 B1
(45) Date of Patent: *Jul. 23, 2002

(54) FLUORESCENT DIAGNOSTIC SYSTEM AND METHOD PROVIDING COLOR DISCRIMINATION ENHANCEMENT

(75) Inventors: Mamoru Kaneko, Hanno; Hitoshi Ueno, Hachioji; Sakae Takehana, Sagamihara; Isami Hirao; Nobuyuki Doguchi, both of Hino; Takeshi Ozawa, Tama; Takefumi Uesugi, Hachioji; Katsuichi Imaizumi, Hachioji; Yasukazu Kogen, Hachioji; Makoto Tomioka, Hachioji; Tadashi Hirata, Hachioji; Masahiro Kawauchi, Hachioji, all of (JP)

(73) Assignee: Olympus Optical Co., Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/153,793

(22) Filed: Sep. 15, 1998

(30) Foreign Application Priority Data

| Sep. 24, 1997 | (JP) | 9-258758 |
| Oct. 2, 1997 | (JP) | 9-270048 |
| Oct. 3, 1997 | (JP) | 9-271580 |
| May 28, 1998 | (JP) | 10-148039 |

(51) Int. Cl.$^7$ ................................................. A61B 1/06
(52) U.S. Cl. ........................ 600/160; 600/478; 600/476
(58) Field of Search .............................. 600/109, 160, 600/476, 478; 250/461.2, 373, 372

(56) References Cited

U.S. PATENT DOCUMENTS

| 4,768,513 A | * | 9/1988 | Suzuki | 600/476 |
| 5,179,598 A | * | 1/1993 | DiFoggio et al. | 382/48 |
| 5,515,449 A | * | 5/1996 | Tsuruoka et al. | 382/128 |
| 5,590,660 A | * | 1/1997 | Macaulay et al. | 600/160 |
| 5,631,734 A | * | 5/1997 | Stern et al. | 250/461.1 |
| 5,647,368 A | | 7/1997 | Zeng et al. | 128/665 |
| 5,749,830 A | * | 5/1998 | Kaneko et al. | 604/109 |
| 5,793,886 A | * | 8/1998 | Cok | 382/169 |
| 5,865,754 A | * | 2/1999 | Sevick-Muraca et al. | 600/476 |
| 6,161,031 A | * | 12/2000 | Hochman et al. | 600/310 |

FOREIGN PATENT DOCUMENTS

| JP | 6-54792 | 3/1994 |
| JP | 8-557 | 1/1996 |
| JP | 9-327433 | 12/1997 |

\* cited by examiner

Primary Examiner—John P. Leubecker
(74) Attorney, Agent, or Firm—Ostrolenk, Faber, Gerb & Soffen, LLP

(57) ABSTRACT

A fluorescent imaging device to prevent the breakdown of a fluorescent image high-sensitivity imaging apparatus has a light source for endoscope use which selectively switches between an excitation light and a white light. This introduces a light into a light guide of an endoscope and such light is emitted onto an object. A fluorescent image high-sensitivity imaging device images the fluorescences obtained by excitation with the excitation light which is emitted onto the object. A white light imaging device images a white light image obtained from the white light which is emitted onto the object. A switch inputs a power source onto the fluorescent image high-sensitivity imaging apparatus and there is a mechanism to prevent overprint on an image plane of the fluorescent image high-sensitivity imaging apparatus which is in the imaging condition with the power source inputted. A fluorescent observation image generating device generates a fluorescent observation image signal for fluorescent observation use, and outputted from the fluorescent image high-sensitivity imaging measure of the imaging part is in electric signal from; which a white light observation image signal used for white light observation is derived.

69 Claims, 15 Drawing Sheets

FIG.4

| SWITCHING CONDITION OF EACH DEVICE | | CAMERA CONDITION |
|---|---|---|
| LIGHT SOURCE DEVICE | CONTROL CENTER | |
| OFF | OFF | INOPERATIVE |
| ON | OFF | INOPERATIVE |
| OFF | ON | WHITE LIGHT MODE |
| ON | ON | WHITE LIGHT MODE |
| ON (PHOTOCOUPLER)- (PHOTOCOUPLER)+ | ON | WHITE LIGHT MODE / FLUORESCENCE MODE |

| SWITCHING CONDITION OF EACH DEVICE | | CAMERA SHUTTER |
|---|---|---|
| LIGHT SOURCE DEVICE | CONTROL CENTER | |
| OFF | OFF | CLOSE |
| ON | OFF | CLOSE |
| OFF | ON | CLOSE |
| ON | ON | CLOSE |
| ON (PHOTOCOUPLER)- (PHOTOCOUPLER)+ | ON | CLOSE |
| | | OPEN |

OBSERVED REGION

FLUORESCENT DIAGNOSTIC SYSTEM AND METHOD PROVIDING COLOR DISCRIMINATION ENHANCEMENT

BACKGROUND OF THE INVENTION

1. Field of the Invention

The present invention relates to fluorescent imaging devices to conduct fluorescent observations by using an endoscope to irradiate an excitation light onto an area of a biological tissue to be examined with such devices being characterized by the ability to switch between fluorescent observation and a conventional reflected light observation.

2. Description of the Related Art

Recently, diagnostic technics have been developed using an endoscope to irradiate tissue to be studied with visible light and to detect resulting fluorescent images which are then analyzed for diagnostic purposes. These technics have been found particularly useful for diagnosing disease conditions such as cancers or tissue degeneration and for highlighting the boundary regions of the conditions under study. These technics are sometimes enhanced by also studying normal light images resulting from reflection of the irradiating visible light (usually white light).

In the case of autofluorescence, i.e., the stimulated emission resulting from impingement of the excitation light onto a biological tissue, the fluorescence typically has a longer wavelength than that of the excitation light. Fluorescent substances within organisms are exemplified by collagens, NADH (nicotinamide adenine dinucleotide), FMN (flavin mononucleotide), pyridine nucleotide and the like. Recently, the relationship between such fluorescent substances and various diseases has been recognized, making it possible to diagnose cancers and the like by these fluorescences.

In addition, certain fluorescent substances such as HpD (hematoporphyrin), Photofrin, ALA (δ-amino levulinic acid), and GFP (Green fluorescent protein), have been found which are selectively absorbed by cancers and thus may be used as contrast materials. In addition, certain fluorescent substances may be added to a monoclonal antibody whereby the fluorescent may be attached to affected areas by an antigen-antibody reaction.

As the excitation lights, for example, lasers, mercury lamps, metal halide lamps and the like are used. For example, when a light with the wavelength of 437 nm is emitted onto a gastrointestinal tract tissue, green autofluorescence by abnormal tissues is attenuated compared to the autofluorescence of normal tissues, but red autofluorescence of abnormal tissues is not attenuated as much compared to the autofluorescence of normal tissues. A transendoscopic fluorescent observation device utilizing this principle to image the green and red fluorescent emission, and to show the existence of abnormal tissues has been disclosed in Japanese Unexamined Patent Publication No. 9-327433.

Since the fluorescent images obtained in this way have very weak intensities compared to the reflected images obtained with conventional white light, photomultiplication, for example, using an image intensifier is necessary.

Generally, when a blue or ultraviolet light is emitted onto biological tissue, an autofluorescence occurs within a longer wavelength band than that of the excitation light. Moreover, fluorescent spectra are different between normal tissues and abnormal tissues such as precancerous tissues, cancerous tissues, inflammatory tissues, and dysplastic tissues so that the existence of lesions and conditions of lesions can be detected based on the changes in delicate coloration of the fluorescent images.

In particular, since with a blue excitation light, the intensity distribution of fluorescence stimulated near the green region, especially that of 490 nm–560 mn, is stronger in normal tissue than in diseased tissue, emissions in the green region and in the red region, e.g., wavelengths in the 620 nm–800 nm region are arithmetically processed to generate two-dimensional fluorescent images, and by these fluorescent images the discrimination between affected areas and normal areas can be achieved.

Video images are produced for diagnostic observation of the autofluorescent emissions, and adjustments are made to the ratio between the video signals corresponding to the green and red fluorescent intensities to allow normal tissues to have a certain color tone. Accordingly, tissue known to be normal is first observed, and the ratios of the red and green emissions are adjusted to establish a reference color tone. Then, after the adjustment of the color tone of the normal parts, the potentially diseased tissue is observed. In this way, the normal parts are designated with a certain color tone and abnormal parts are designated with different color tones from that of the normal parts due to the attenuation of the green signal. By the differences in color tones between abnormal and normal parts, the abnormal parts can be visualized. Typically, the ratio is adjusted so that the normal tissue appears a cyanic color tone and diseased tissue appears a red color tone.

Moreover, in a fluorescent observation device of Japanese Unexamined Patent Publication No. 8-557, a single light source is used both as an excitation light to conduct fluorescent observations and as a white light to conduct white light observations by insertion and removal of a filter. Endoscopes usually also include an emergency light source which permits safe removal of the instrument in case of failure of the main light source.

As will be understood, when only fluorescent images are desired, there should be no illumination by white light, but only by the excitation light. Thus, switching is required so that when a white light image is to be obtained, a white light is emitted, and when a fluorescent image is to be obtained, an excitation light is emitted.

Also, switching is controlled so that, when white light is emitted, the resulting image is provided only to a white image imaging device, and when the excitation light is emitted, the fluorescent image is provided only to the high-sensitivity fluorescent imaging device. However, with conventional fluorescent imaging devices, since the endoscope is out of the body when power is applied, if the device is accidently set in its fluorescent observation mode, ambient light may impinge on the fluorescent imaging device. Then, an excess of light enters the image intensifier, and overprint at the high-sensitivity imaging plane of the image intensifier occurs, resulting in its breakdown.

Also with the fluorescent observation device of said Japanese Unexamined Patent Publication No. 8-557, in the case of lamp failure during fluorescent observation, the emergency light provides insufficient luminous energy to excite the tissue sufficiently, making it difficult to observe fluorescence. In addition, even with the emergency light, if the filter for excitation light generation is carelessly removed from in front of the emergency light, the image intensifier will be burnt.

Moreover, since the delicate variations in coloration of fluorescent images are subjectively visualized by the operator, the lack of fixed discrimination standards makes it difficult to compare of findings by different users, and at different facilities such as hospitals.

Also in the conventional example in Japanese Unexamined Patent Publication No. 9-327433, since adjustment of color tone for normal parts is performed on the individual judgment of the user, the absence of fixed calibration standards renders objective diagnosis by color tone difficult.

SUMMARY OF THE INVENTION

One object of the present invention is to provide a fluorescent imaging device which protects a fluorescent image high-sensitivity imaging measure even under a transitional condition such as at the power input.

Another object of the present invention is to provide a fluorescent imaging device which prevents damage to the high-sensitivity camera if the normal emitting lamp fails during a fluorescent observation and is replaced by the emergency light.

Still another object of the present invention is to provide a fluorescent imaging device which objectively discriminates against delicate changes in coloration of fluorescent images so that an operator can easily visualize the existence of lesions and conditions of the lesions.

A further object of the present invention is to provide a fluorescent imaging device which adjusts the color tone of normal tissues to a desired tone by conducting a simple operation during the observation of the normal tissue, while displaying the color tone of abnormal tissue in contrast with the color tone of the normal tissues.

The fluorescent imaging device of the present invention has a light source, which selectively switches between an excitation light and a white light, introduces the light into a light guide, and then emits the light onto the tissue being inspected; a high-sensitivity fluorescent device for fluorescent images; a white image imaging device for white light images; a device which couples the fluorescent image to the fluorescent imaging device, a device which prevents overprint on the high-sensitivity imaging plane of the fluorescent imaging device, a visible image generation device which generates an electric signal output from the fluorescent imaging device, and a separate visible image generation device which generates an electric signal output from the white light image imaging device.

BRIEF DESCRIPTION OF THE DRAWINGS

A first embodiment of the present invention is illustrated in drawings FIGS. 1–4 where:

FIG. 4 is a table which illustrates the relationship between switching conditions of each device and imaging conditions of the camera;

Figure 5:
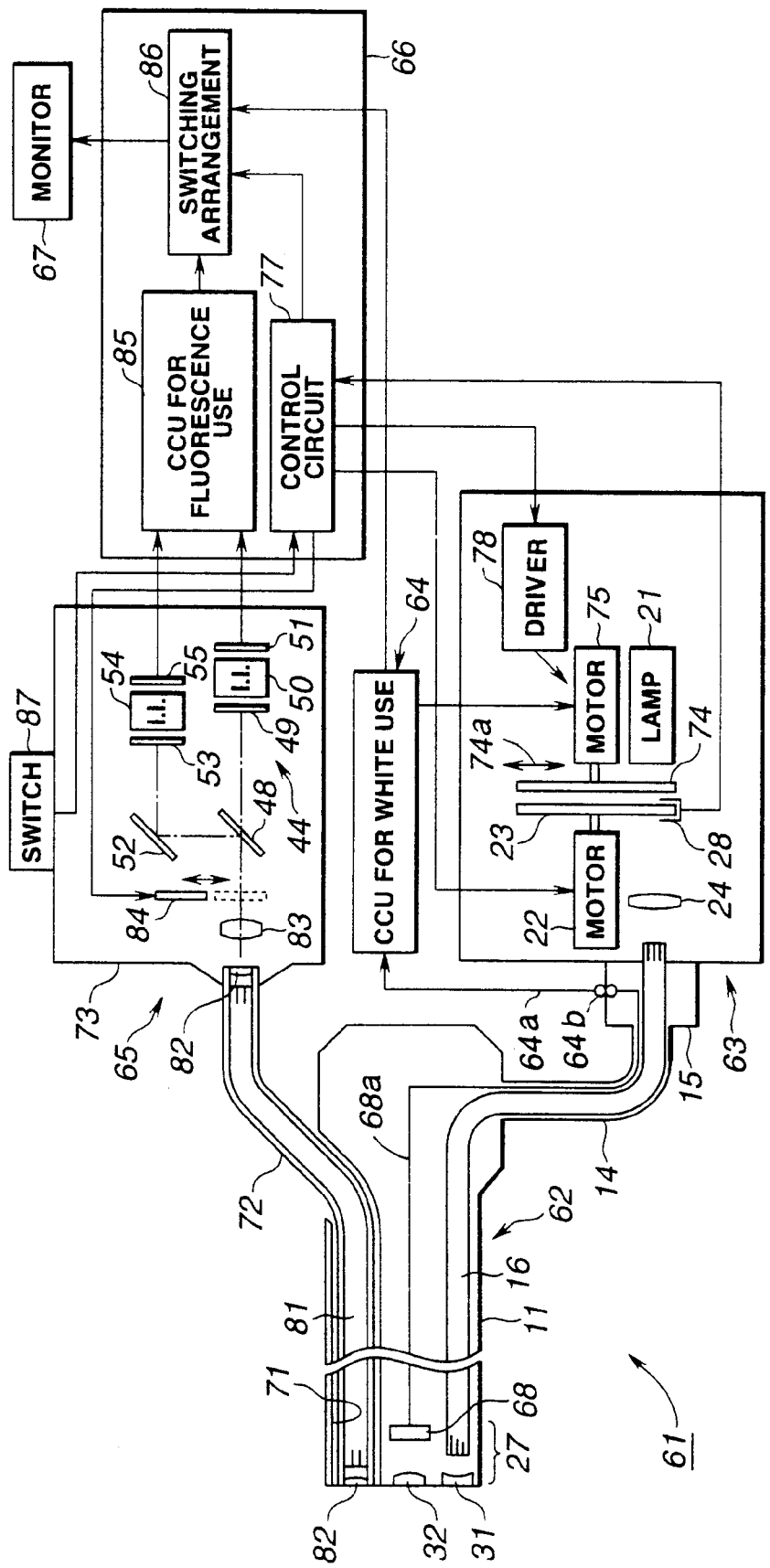
Figure 6:
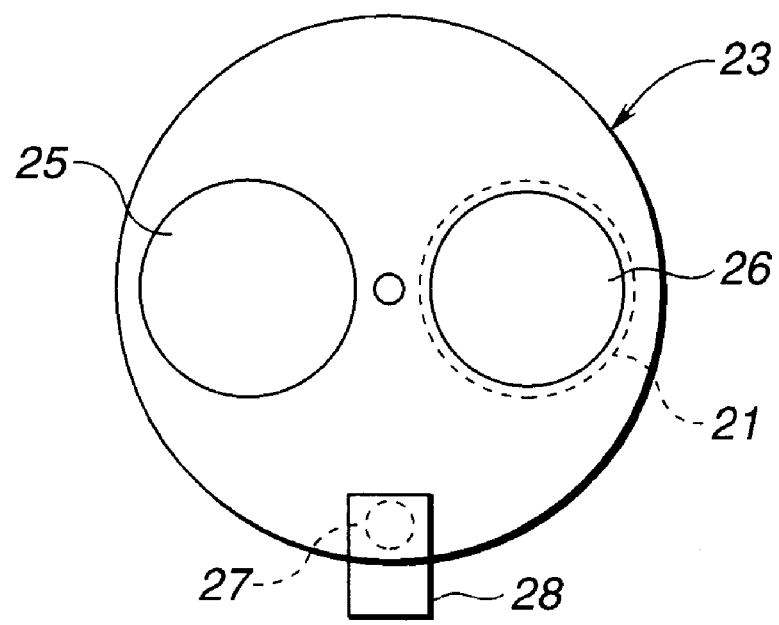
Figure 7:
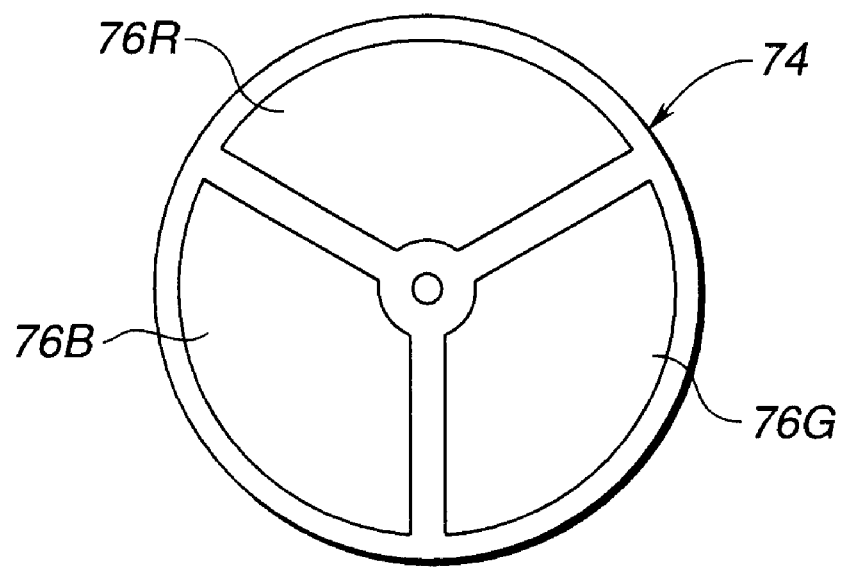
Figures 8, 9:
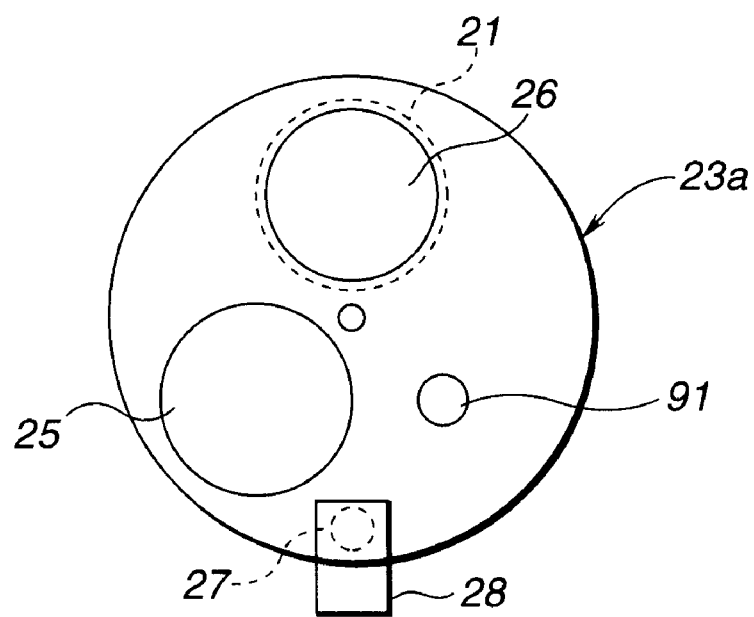
Figure 10:
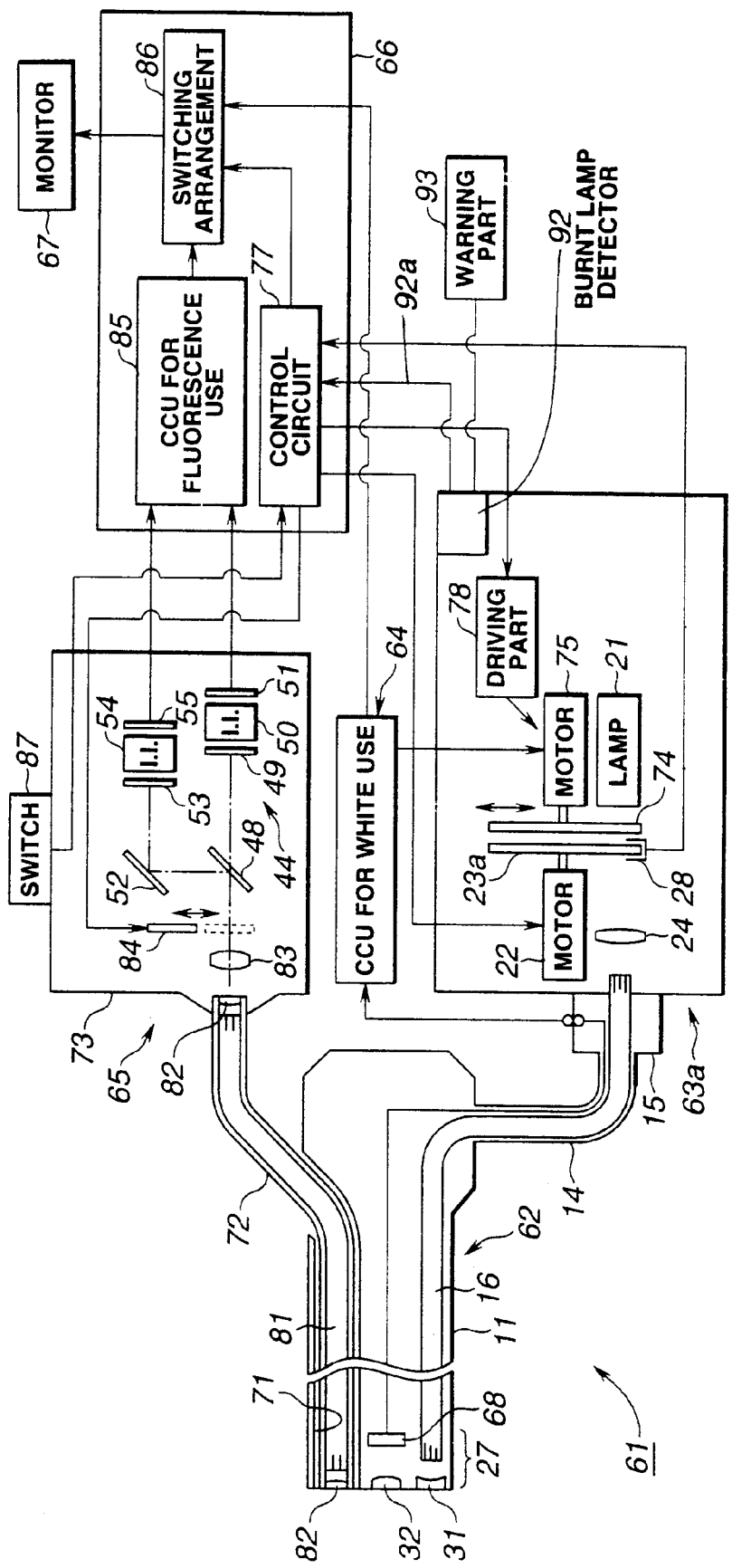
Figure 11:
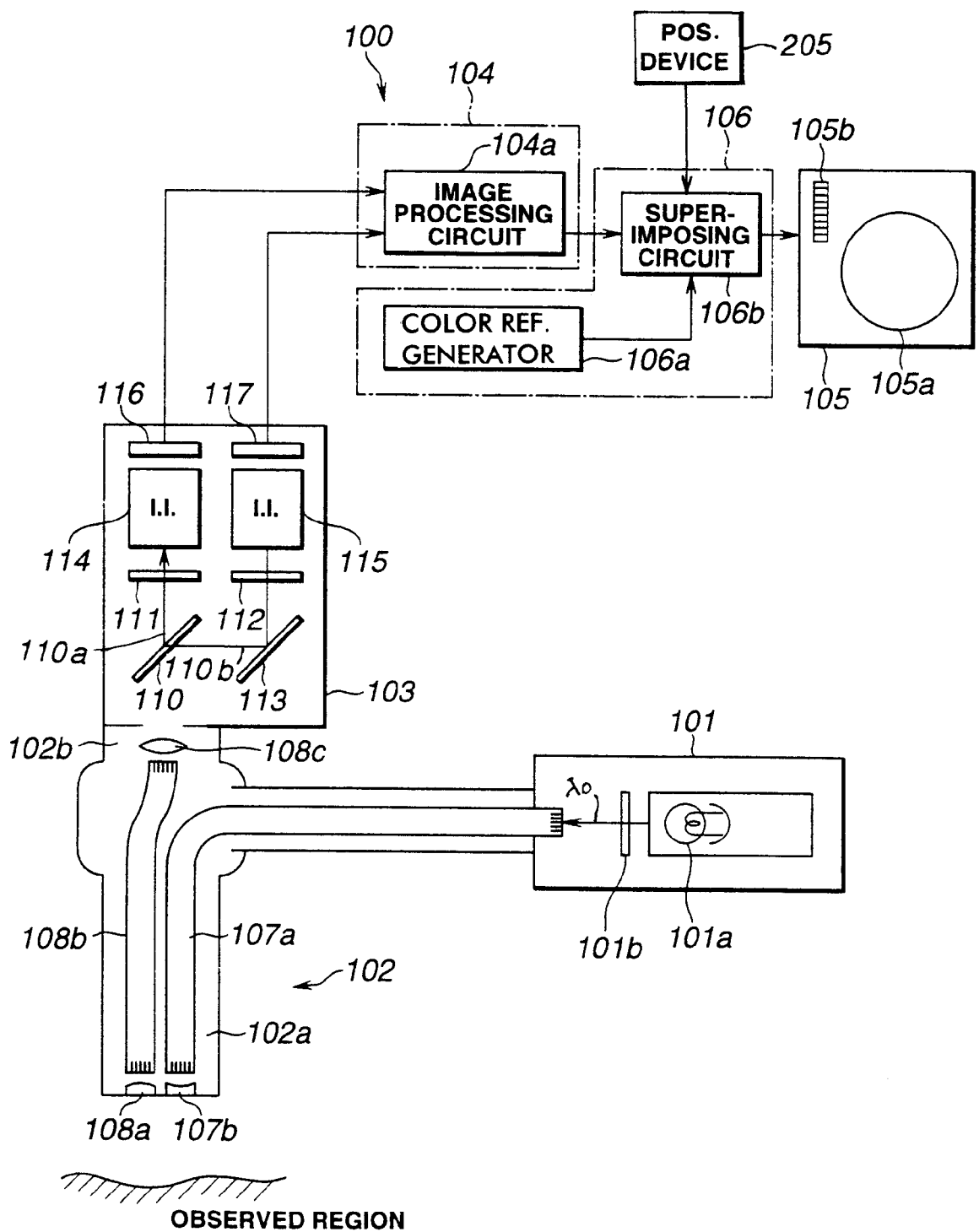
Figure 12:
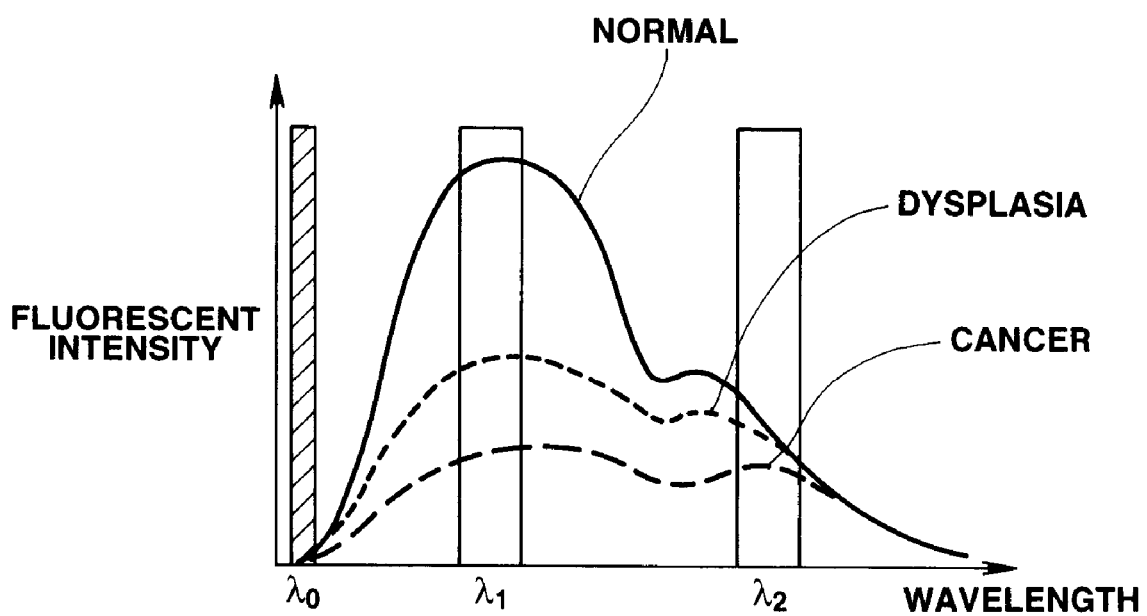
Figure 13:
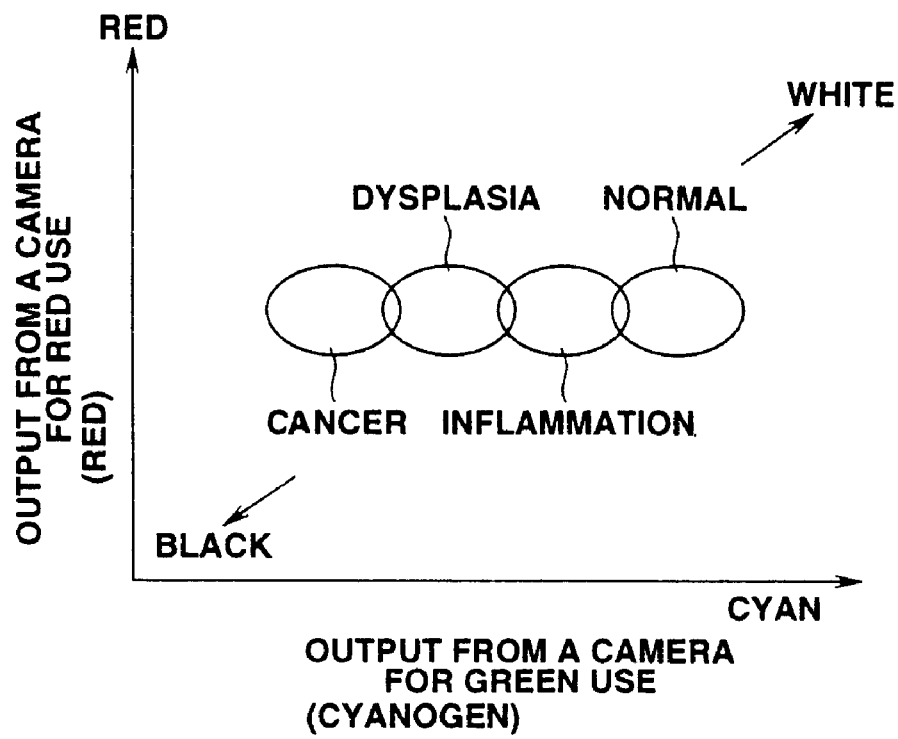
Figure 14:
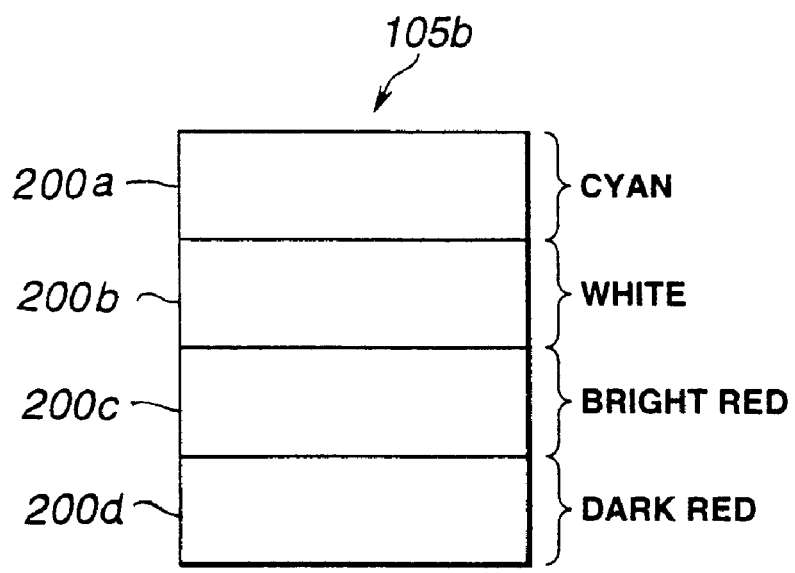
Figure 15:
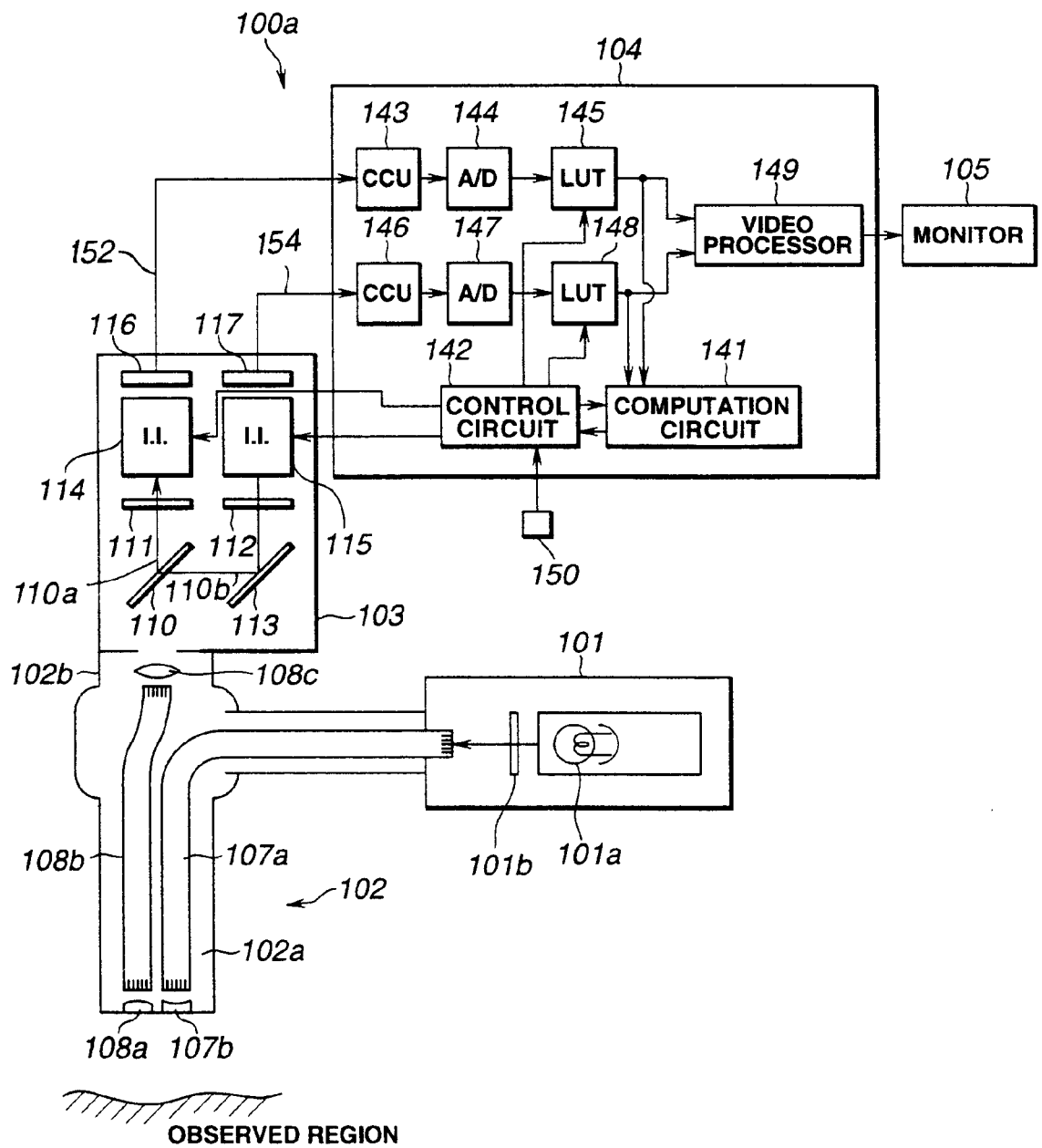
Figure 16A:
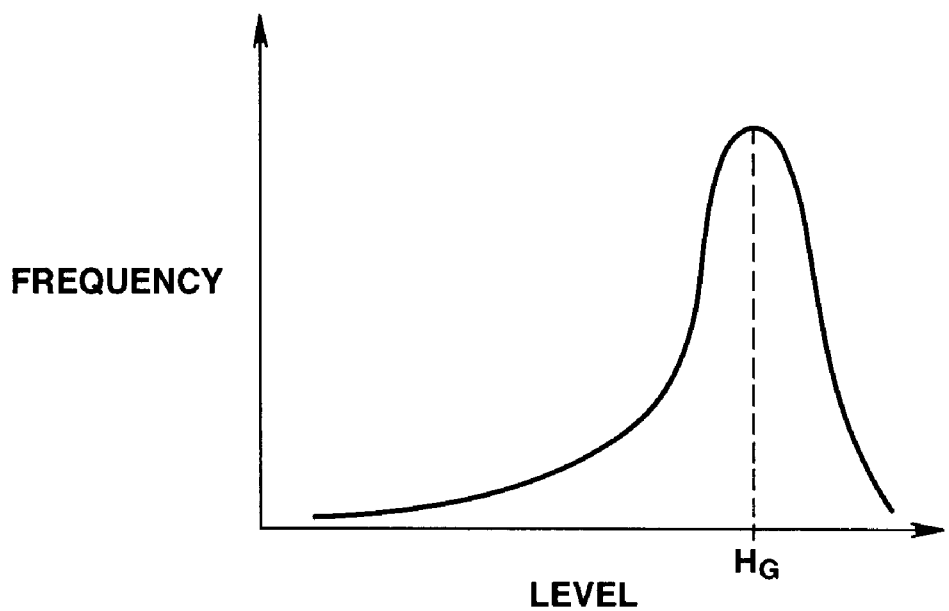
Figure 16B:
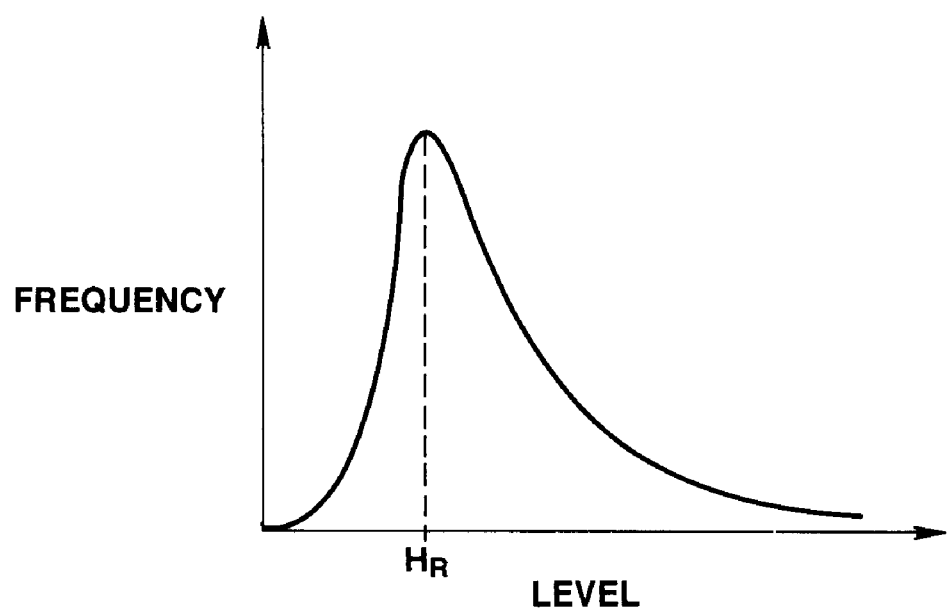
Figure 17:
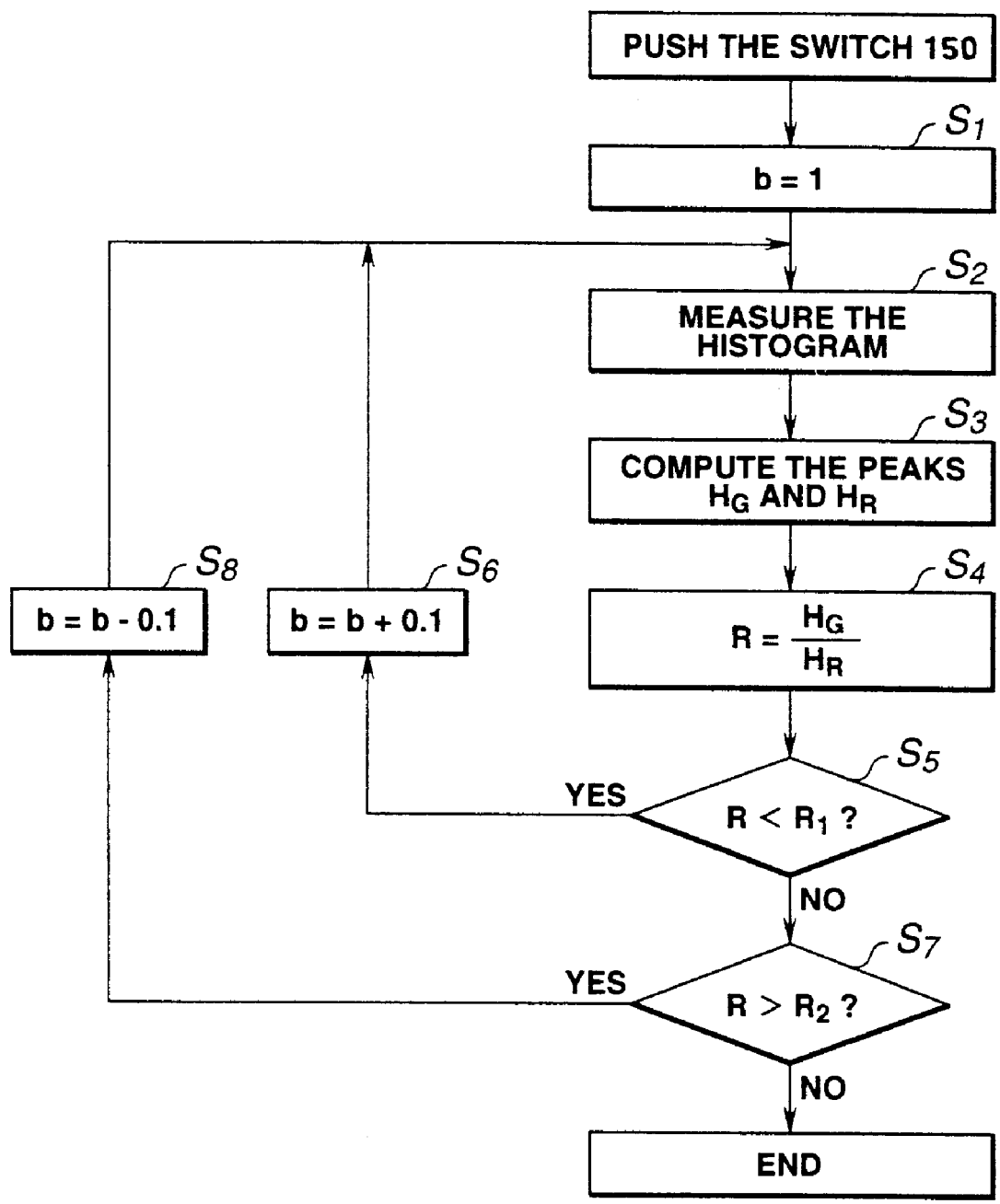

A second embodiment of the present invention is illustrated in drawing FIGS. 5–8 where:

FIG. 5 is a structural schematic of an endoscopic fluorescent imaging device;

FIG. 6 is a front elevation which illustrates structure of the rotary filter that is not illustrated in FIG. 5;

FIG. 7 is a front elevation which illustrates an RGB rotary filter;

FIG. 8 is a table which illustrates the relationship between switching conditions of each device and shutter conditions of the camera;

A third embodiment of the present invention is illustrated in drawing FIGS. 9 and 10 where:

FIG. 9 is a front elevation of another rotary filter;

FIG. 10 is a structural schematic of the fluorescent observation device;

A fourth embodiment of the present invention is illustrated in drawing FIGS. 11–14 where:

FIG. 11 is a structural schematic of the fluorescent image device of the fourth embodiment;

FIG. 12 is a spectrum atlas of the fluorescences emitted from normal and abnormal tissues;

FIG. 13 is a color distribution diagram showing the relationship in coloration between the normal part and the lesion parts in fluorescent color observation images:

FIG. 14 is a schematic diagram that illustrates one structural example of the color index;

A fifth embodiment of the present invention is illustrated in drawing FIGS. 15–17 where:

FIG. 15 is a structural schematic of the structure of the fluorescent image device of the fifth embodiment;

FIG. 16A is a histogram showing the frequency of the green image signal level;

FIG. 16B is a histogram showing the frequency of the red image signal level; and FIG. 17 is a flowchart which illustrates the operations to set normal tissues to a certain tone.

Figure 18:
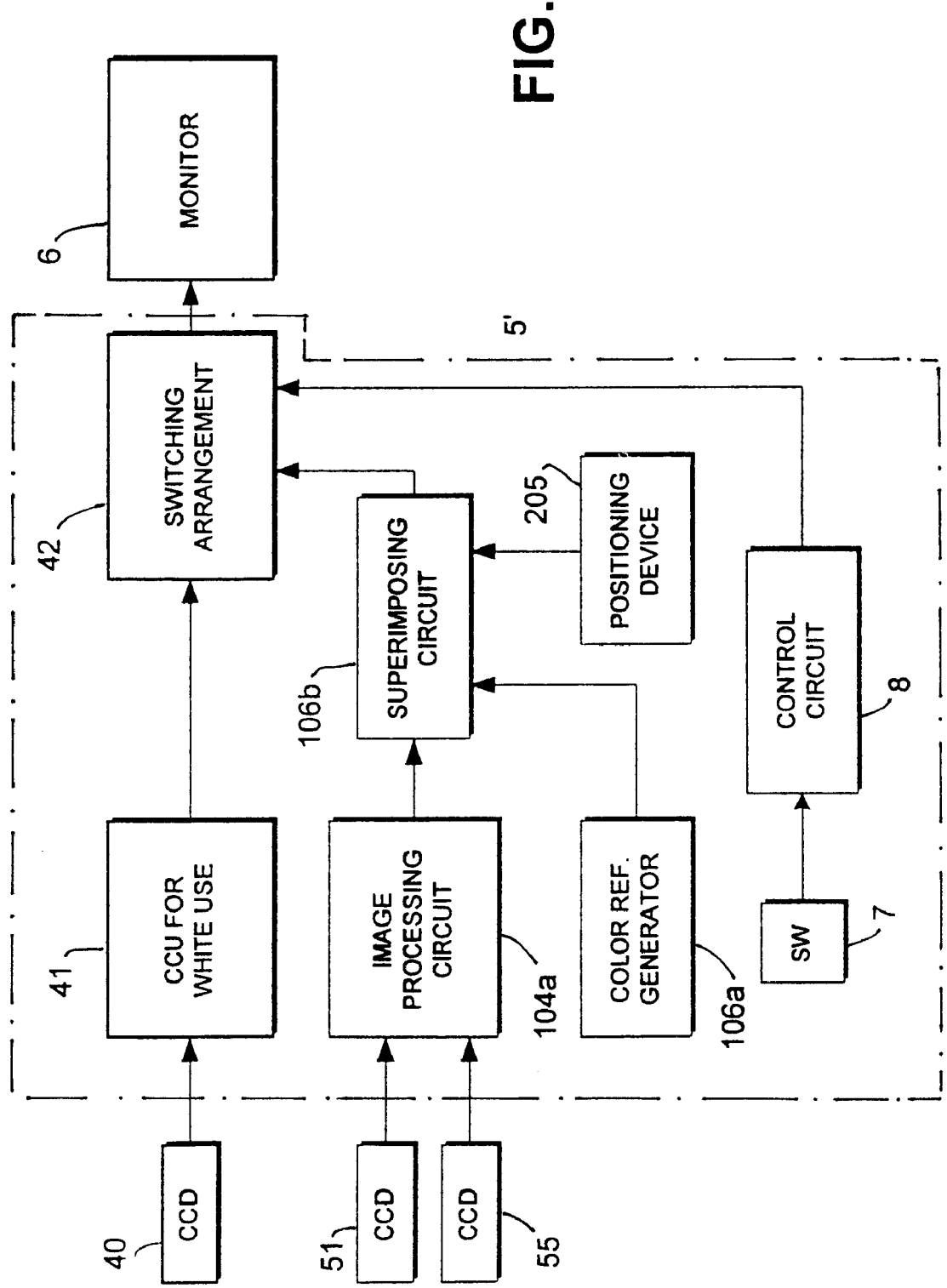

FIG. 18 is a schematic diagram of a sixth embodiment of the present invention.

Figure 19:
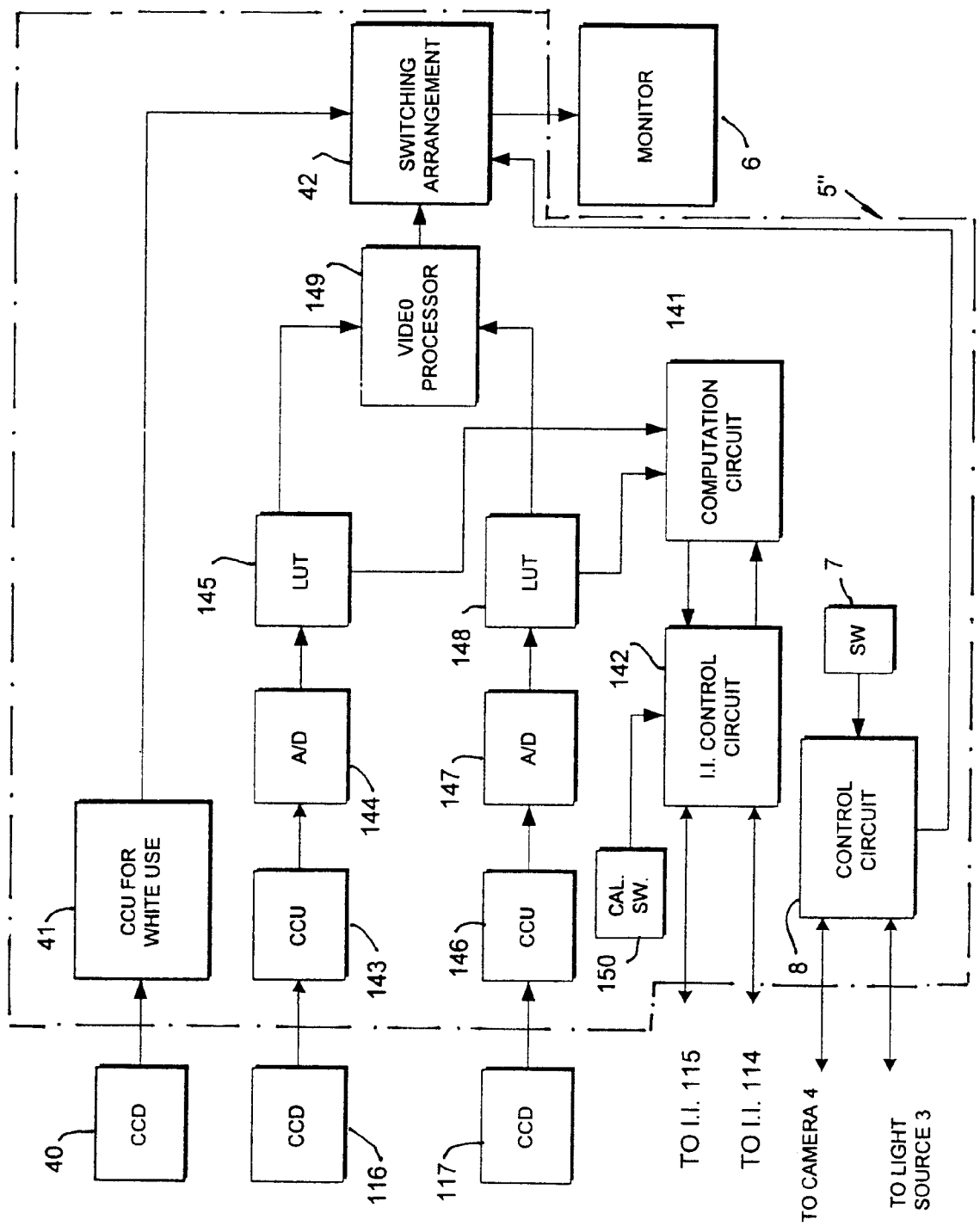

FIG. 19 is a schematic diagram of a seventh embodiment of the present invention.

DESCRIPTION OF THE PREFERRED EMBODIMENTS

The first embodiment of the present invention will now be described with particular reference to FIGS. 1–4.

The fluorescent imaging device of this embodiment has an imaging camera including a white light imaging device and a high-sensitivity fluorescent imaging device, a device to couple a power source to the camera, and an overprinting prevention device to protect the high-sensitivity imaging plane by controlling a movable mirror on an optical path so that under the imaging condition where the power source is ON, imaging by the fluorescent imaging device is prevented.

Figure 1:
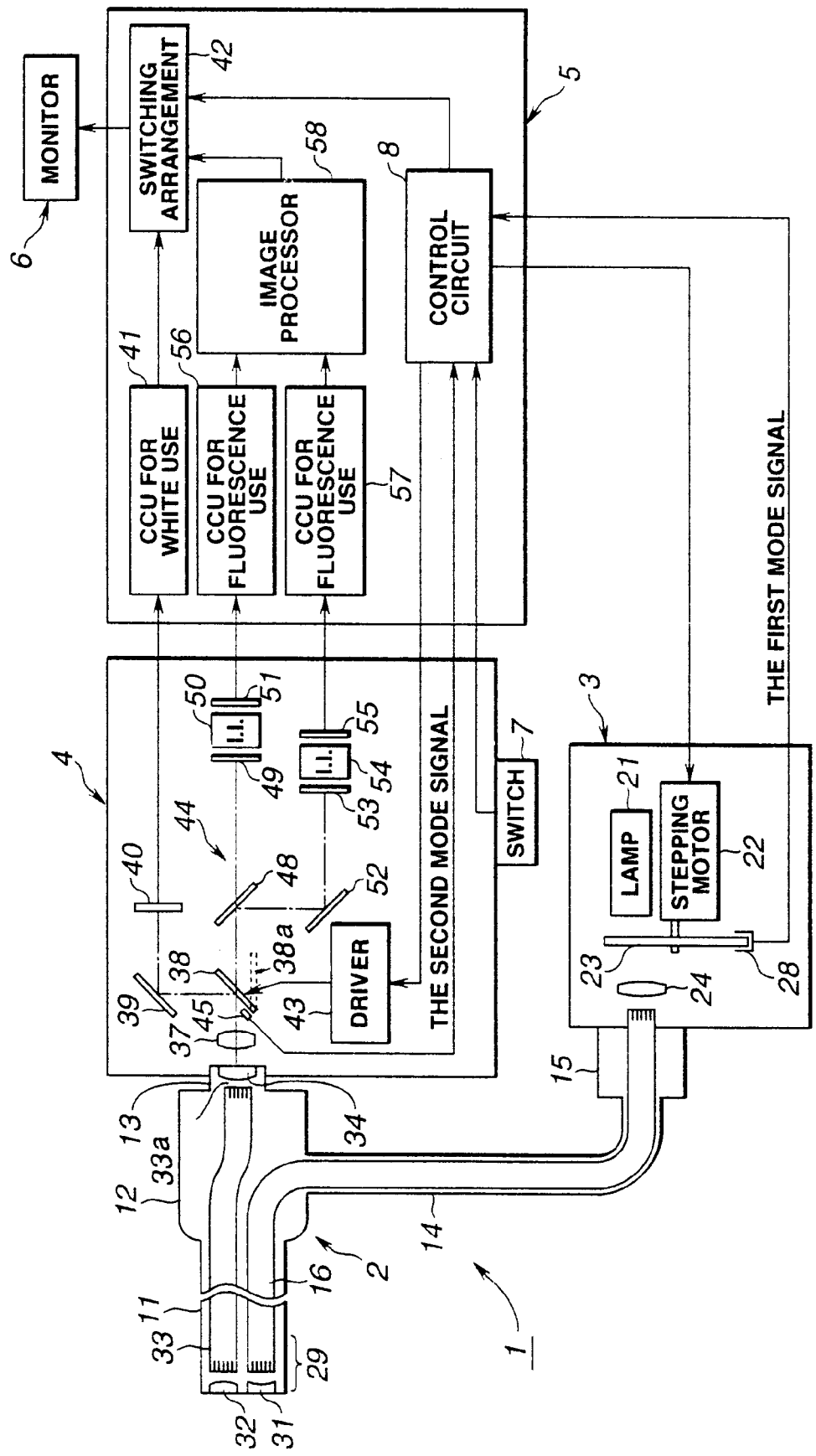
FIG. 1 is a structural schematic of an endoscopic fluorescent imaging device.

As shown in FIG. 1, the fluorescent imaging device 1 comprises an optical endoscope 2 which is inserted into the body under examination, a light source 3 which supplies an illumination light to the endoscope 2, an imaging camera 4, including an integrated imaging device which can be removably attached to the endoscope 2, a control center 5 which conducts signal conditioning for the imaging device in the camera 4, and a monitor 6 which provides a visible image for diagnostic observation.

A switch 7 on camera 4 is provided to operate a control circuit 8 in control center 5. Control circuit 8 controls the operation of light source 3 and camera 4 to provide the desired light source, to prevent impingement of white light on the fluorescent image detectors, and, by means of a switching arrangement 42, to provide either a signal representing either the fluorescent image or the white light image to monitor 6.

Endoscope 2 has a slender insertion part 11, an operation part 12 at the back end of the insertion part, an eyepiece part 13 at the back end of the operation part 12, and a light guide cable 14 which extends from the operation part 12. A connector 15 removably couples light source 3 to the end of light guide cable 14.

A light guide 16 which functions to conduct the incoming white light or excitation light, is inserted in insertion part 11, operation part 12, and light guide cable 14. By installing connector 15 onto light source device 3, the white light or the excitation light is provided from the light source device 3 to light guide 16.

As an illumination light source 2 such as a metal halide lamp or the like is provided in light source device 3. The white light emitted from this lamp 21 passes through a rotary filter 23 which is rotated by a stepping motor 22, and then is supplied to the light admittance end of the light guide 16 through a condensing lens 24.

Figure 2:
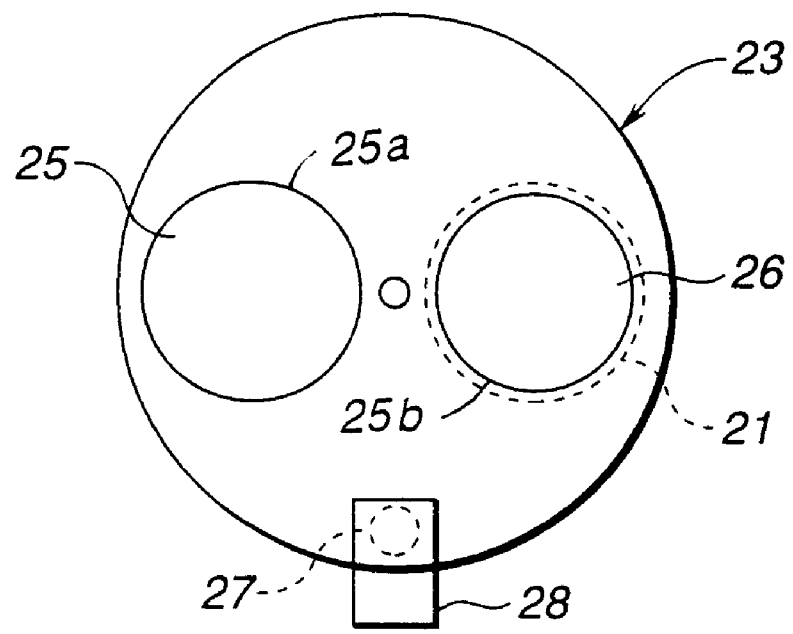
FIG. 2 is a front elevation which illustrates one structural example of the rotary filter.

As shown in FIG. 2, rotary filter 23 is disk shaped, and includes a first circular aperture 25A and a second circular aperture 25B. A clear glass insert 25 may be provided in aperture 25A if desired. Second aperture 25B is fitted with a blue filter 26 which passes the excitation light with a wavelength in a narrow-band of the blue region, preferably about 400–450 nm. When aperture 25A is positioned in front of light source 21 white light is supplied into light guide 16, and when the blue filter 26 is positioned in front of light source 21 (as shown in FIG. 2), blue light for fluorescent observation is supplied into the light guide 16.

The rotational position of the stepping motor 22 is controlled by control circuit 8. Moreover, a small opening 27 is formed at the circumference of rotary filter 23, and a photo coupler 28 is disposed so that it spans across the circumference. When the photo coupler 28 detects the hole 27, it provides a position detection signal indicating that the blue filter 26 is positioned on the optical path.

As shown in FIG. 1, photo coupler 28 includes a light source and a light detector (not shown) disposed on opposite sides of the rotary filter 23. When filter 26 is aligned with light source 21, hole 27 is positioned between the light source and the detector of photo coupler 28, allowing light to pass through from the light source to the detector.

The light detector is coupled to control circuit 8.

A power switch (not shown) is provided for light source 3. When this switch is turned ON, power is supplied to lamp 21 and to stepping motor 22, which starts to rotate filter 23.

The light which is transferred by light guide 16 is emitted onto the tissue under examination, such as an organ of a body cavity, through the illumination lens 31 which provides an illumination window at the tip part 29 of the insertion part 11.

An objective lens 32 which provides an observation window is installed near to lens 31. This focuses an image, either reflected white light or a fluorescent image resulting from the excitation light, on an image plane at the tip of the image guide 33. The image which is formed on the tip plane of image guide 33 is transferred onto the back end plane 33A of the image guide 33. A magnified view of the image provided by light guide 33 is available through an eyepiece lens 34 of an eyepiece part 13 which is positioned adjacent to the back end plane of the image guide 33. This image may be viewed by the naked eye when camera 4 is not attached to endoscope 2.

When the camera 4 is mounted onto the eyepiece part 13, the image-forming lens 37 within the camera is disposed opposite to eyepiece lens 34.

On the resulting optical path, within camera 4, is a movable mirror 38, which is movable between the position shown in FIG. 1 and the position 38A shown in outline. When it is in the position shown, light focused by lens 37 is reflected to impinge on a second fixed mirror 39, so that the light which is reflected from movable mirror 38 is also reflected by mirror 39, to form an image on the imaging plane on a first charge coupled device (CCD) 40 which services the white light imaging device.

The optical image which impinges on CCD 40 is converted to an electrical signal and is coupled to a first camera control unit (CCU) 41. This converts the input electrical signal into video signal for display on monitor 6 through a switching arrangement 42 when the tissue is being examined under white illumination. Movable mirror 38 is driven by a driver controlled by control circuit 8. For the white light observation mode, mirror 38 is in the position shown in solid lines and the light focused by lenses 34 and 37 is coupled to white light image imaging device 40. For the fluorescent observation mode, a control signal sent from control part 8 to driver 43 causes movable mirror 38 to be set in the position shown by dotted lines. Then, light which goes through lenses 34 and 37 is coupled to fluorescent imaging device 44.

Figure 3:
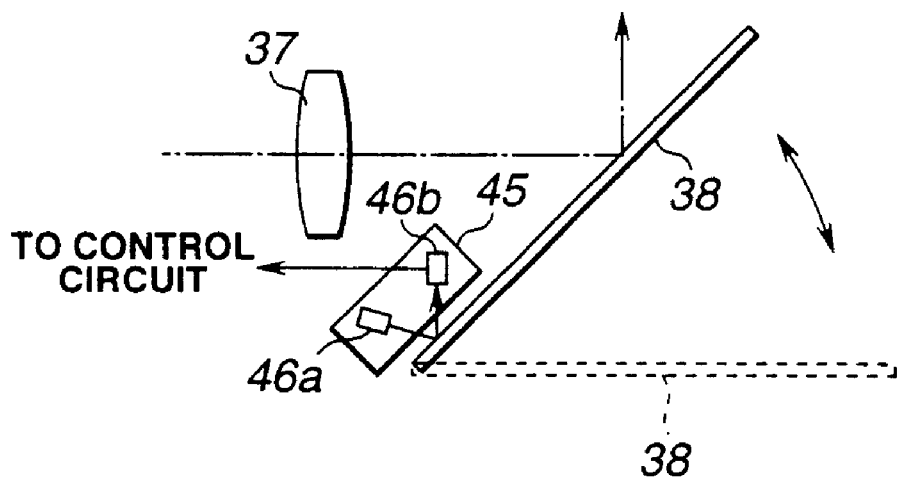
FIG. 3 is an enlarged section of the structure around the movable mirror.

The position of movable mirror 38 is detected by a photoreflector 45. As shown in FIG. 3, the luminous element 46a and the light detector 46b which form photoreflector 45 are disposed opposite to the plane of, for example, the proximal end of movable mirror 38. Thus, when mirror 38 is in the position shown with the solid line, the output signal of light detector 46b is provided as the second mode signal (see FIG. 1) to control circuit 8.

Fluorescent imaging device 44 comprises a dichroic mirror 48 which is inclined at 45 degrees on the optical path. Dichroic mirror 48 selectively reflects red light but transmits the rest of the visible spectrum.

The light transmitted by dichroic mirror 48 then passes through a green filter 49 which selectively transmits the light with green wavelengths to an image intensifier (I.I.) 50. The green light is amplified by I.I. 50 to form an image on an imaging plane 51 of the CCU for fluorescence use 56.

The light which is reflected by dichroic mirror 48 is further reflected at a mirror 52 and then, passes through a red filter 53 which selectively transmits light with red wavelengths, to an I.I. 54. The red light then is amplified at I.I. 54 to form an image on the imaging plane 55 of the CCU for fluorescent use 57.

The outputs of CCU 56 and 57 are converted into a video display signal by an image processing device 58. The video signal is coupled to monitor 6 through the switching arrangement 42 described below.

Switching arrangement 42 is controlled by the control circuit 8 in conjunction with switch 7 which allows the operator to select a mode of operation, i.e., white light imaging fluorescent imaging or simultaneous white light and fluorescent imaging.

As previously noted, power for camera 4 is supplied by control center 5. When the power is first turned ON, the control circuit 8 goes into operation ahead of other parts. Specifically, the control circuit 8 confirms that the power is present prior to operating a relay which supplies power to the other circuits.

Thereafter, control circuit 8 determines the position of movable mirror 38 at its initial condition. If in error 38 is found to be in the position shown by the solid lines and the camera 4 is not operation, control circuit 8 operates driver 43 to set mirror 43 in the position shown by the dotted lines. In this way, even if a transitional condition exists (e.g., if light source 3 is ON and filler 23 is set to emit white light, when the power source of the control center 5 is turned ON), white light will not impinge on fluorescent imaging device 44.

In addition, when the power for control center 5 is turned OFF, a shut down operation is initiated on which driver 43 is disabled. This again prevents white light from impinging on the fluorescent imaging device 4.

Also, control circuit 8 monitors the ON/OFF condition of the power for lamp 21. When the power for light source 3 is turned ON, after a delay to allow the power source to reach a stable state, control circuit 8 operates stepping motor 22 with reference to a feedback signal provided by photo coupler 28 and also operates movable mirror 38 through driver 43. During the start-up delay, control circuit 8 retains mirror 38 in the position shown by the solid lines. Thereafter stepping motor 22 and driver 43 are operated to select the desired color for the light supplied by filter 23 and the optical path for light collected by image guide 33, in accordance with the position of switch 7.

When the power for light source device 3 is turned OFF, the control circuit 8 immediately disables driver 43, which sets movable mirror 38 into the position shown by the solid lines. This prevents admittance of light to the fluorescent imaging device 44, and thereby prevents damage to I.I.s 50 and 54.

Now, the operation of this first embodiment will be explained.

The sequence of operation for camera 4 from the condition in which the power for light source 3 and control center 5 are both OFF to the condition in which both are turned ON is illustrated with reference to FIG. 4.

When the power for both light source 3 and control center 5 is OFF, neither the white light nor fluorescent light is emitted into the camera 4, and operating power is not supplied to the imaging devices of camera 4. Therefore, the camera 4 is in the "inoperative" condition as shown in FIG. 4.

When the power for light source 3 is turned ON, but the power for control center 5 is still OFF, although the white light or the fluorescent light is ready to be emitted into the camera 4, operating power is not supplied to the imaging devices and camera 4 is still in the "inoperative" condition as shown in FIG. 4.

If the power for light source 3 is OFF but the power for control center 5 is turned ON, at first, neither reflected white light nor stimulated fluorescent light is coupled to the camera 4. Nevertheless, since operating power is supplied to both of the imaging devices, movable mirror 38 is set at the position shown by the solid lines, and the camera 4 is set to operate in the "white light mode," as indicated in FIG. 4.

If power is supplied to both light source device 3 and control center 5, during the start up delay, movable mirror 38 is set at the solid line position so that even through both of imaging devices are energized, camera 4 is still in "the white light mode."

After the start-up delay, if white light imaging is selected by switch 7, the control circuit 8 controls the rotation of the stepping motor 22 and positions a clear glass insert 25 in the optical path of lamp 21, and confirms the position of filter 23 by detection of a signal from photo coupler 28. If the level of the detection signal indicates that the detector in photo coupler 28 is not energized, control circuit 8 keeps the movable mirror at the solid line position.

Then, white light from lamp 21 is transmitted through clear glass insert 25 in aperture 25a of filter 23, and passes light guide 16 to illumination lens 31 to illuminate the tissue under examination.

The light which is reflected from the tissue under examination is focused at the tip plane of the image guide 33 by the objective lens 32, is transferred onto the back end plane of the image guide 33, is reflected at the movable mirror 38 and is then imaged at the CCD for white use 40.

The output signal of this CCD for white use 40 undergoes signal conditioning at the CCU for white use 41 and is converted into a picture signal, which is displayed as a white light image on the monitor 6 through switching arrangement 42.

On the other hand, if the fluorescent imaging mode is selected by switch 7, the control circuit 8 controls the rotation of the stepping motor 22 and positions the blue filter 26 on the optical path, while confirming the position by the detection signal of the photo coupler 28. When the detection signal indicates that the blue filter is in the proper position, control circuit 8 operates driver 43 to switch movable mirror 38 to the dotted line position, thereby enabling the "fluorescent mode."

With the blue filter in front of lamp 21, only light components with blue wavelengths are transmitted through light guide 16, to illuminate the tissue under examination.

The fluorescence generated by the blue excitation light is focused onto the tip plane of image guide 33 by objective lens 32, is transferred onto the back end plane of the image guide 33, and then impinges on dichroic mirror 48 within the camera 4. The light transmitted by dichroic mirror 48 passes through green filter 49, is amplified by I.I. 50, and imaged at the CCD for fluorescence use 51.

On the other hand, the light reflected by dichroic mirror 48 is further reflected by mirror 52, passes through red filter 53, is amplified by I.I. 54 and is imaged at the CCD for fluorescence use 55.

The output signals of CCDs for fluorescent use 51 and 55 undergo signal conditioning at the CCUs for fluorescent use 56 and 57, respectively, and are converted into picture signals. Then, image processing such as adjustment of intensity of the images, image component registration and the like is performed by image processing device 58, and, both images are superimposed with different colors and displayed as a fluorescent image on the monitor 6 through the switching arrangement 42.

If combined white light and fluorescent imaging is selected by switch 7, the control circuit 8 rotates the stepping motor 22 at a constant speed. Then as shown in FIG. 2, when the detection signal of the photocoupler 28 indicates that the blue filter 26 is disposed on the optical path, control circuit 8 operates driver 43 to switch the position of the movable mirror 38 from the solid line to the position to the dotted line position, and conducts the fluorescent imaging as described above, and then stores the fluorescent image in a memory circuit (not shown) within image processing device 58.

When blue filter 26 is rotated away from lamp 21 by stepping motor 22, the control circuit 8 disables driver 43, and movable mirror 38 moves from the dotted line position to the solid line position to permit white light imaging. The resulting white light image is stored in a memory circuit (not shown) in the CCU for white use 41.

Thereafter filter 23 rotates further, and clear glass 25 withdraws from the optical path. When the blue filter 26 is again positioned in the optical path, as indicated by the detection signal of the photocoupler 28, the control circuit 8 operates driver 43 to switch the position of the movable mirror 38 back to the dotted line position. In this way, the movable mirror 38 is switched into the fluorescent imaging condition and conducts the fluorescent imaging of the next frame, and then stores the fluorescent image in memory within the image processing device 58. In this way, both images of each frame, namely the white light image and the fluorescent image are sequentially obtained and stored into the memory.

By operating switching arrangement 42 alternatively with appropriate time intervals, control circuit 8 allows the white light image and the fluorescent images to be alternatively displayed on monitor 6.

Alternatively, by shifting the timing between reading the memory of the CCU for white use 41 and reading the memory of the image processing device 58, both images may be displayed simultaneously on monitor 6.

Thus, according to this embodiment, before a certain operation mode is set, such as during the start-up delay excessive light is prevented from impinging on fluorescent imaging device 44 to protect the high-sensitivity image plane from overprinting, with a consequent breakdown of the I.I.s 50 and 54 caused by the admittance of excessive light.

Even during a transitional condition of switching from the fluorescent imaging mode to the white light imaging mode, the imaging circuits are switched before the condition of the light source device 3 is shifted from the emitting of the excitation light to the radiation of the white light.

In addition, when switching from the white light imaging mode to the fluorescent imaging, the imaging circuits are switched after the light source 3 is switched from white light to the excitation light, so a breakdown of the I.I.s 50 and 54 caused by admittance of excessive light into the fluorescent imaging device 44 is prevented.

Although photocoupler 28 detects that the blue filter 26 is positioned on the optical path as shown in FIG. 2, a second photocoupler may be provided to detect that the clear glass insert 25 is positioned on the optical path. Thus, by detecting signals from these two photocouplers, the rotary operation of the stepping motor 22 and the operation of the movable mirror 38 can be controlled with greater certainty.

Moreover, although in this embodiment, where movable mirror 38 is positioned on the optical path when the power source of control center 5 is turned ON, the admittance of the light to the fluorescent imaging device 44 is prevented so that the damage to the I.I.s 50 and 54 that would be caused by the admittance of an excessive light or the like, is prevented. Also, the fluorescent imaging device 44 may be in the non-imaging condition by controlling the operating power source to the I.I.s 50 and 54, to provide further protection.

For example, when the switch for the power source of the control center 5 is turned to be ON, the control circuit 8 may detect the condition of the light source 3 so when light source 3 is turned ON, unless the blue filter 26 is set on the optical path, as indicated by the output of the photocoupler 28, operating power would not be supplied to the I.I.s 50 and 54.

In this case, for example, when the power source for control center 5 is turned ON but the power for light source 3 is kept OFF, the non-imaging condition is established, but even if the power for light source 3 is turned ON, only if the blue filter 26 is disposed on the optical path, is operating power supplied to the I.I.s 50 and 54.

Moreover, when rotary filter 23 is rotated to shift clear glass insert 25 into position on the optical path, until it is actually positioned on the optical path, as indicated by the detection signal from the photocoupler 28, the non-imaging condition is not established where the operating power source is supplied to the I.I.s 50 and 54. By establishing this non-imaging condition, the breakdown due to the excessive admittance of the light into the I.I.s 50 and 54 can be prevented, which breakdown could possibly occur when the fluorescent imaging mode is still maintained during the switching operation. When switching from the white imaging mode to the fluorescent imaging mode condition, the breakdown of the I.I.s 50 and 54 can similarly be prevented.

Instead of controlling the operation power source to the I.I.s 50 and 54, by decreasing the sensitivities of the I.I.s 50 and 54, a condition may be set where even if light having an intensity that far exceeds that of fluorescence enters the fluorescent imaging device 44, no overprint can occur and breakdown is prevented.

In addition, provision may be made to control the light source 3 which emits the excitation light and the white light to be the initial condition where the excitation light is secured to be emitted when, for example, the power source of the light source device is turned to be ON. In this way, even with a camera which is intended only for fluorescent imaging, and has no provision to protect the fluorescent imaging device 44, damage which might result if the power for the camera is turned ON before the camera is set to the proper condition for use can be prevented.

The second embodiment of the present invention is illustrated with reference to FIGS. 5 to 8.

In this embodiment, the endoscope is an electronic endoscope which integrates a white light image imaging device at its tip, where a fluorescent image introducing part of a fluorescent imaging device is inserted into a forceps channel of this electronic endoscope, a fluorescent image which is introduced through his fluorescent image introducing part is imaged at the fluorescent imaging part, and then the signals are processed in, for example, a CCU for fluorescent use within a control center so that a white light image and a fluorescent image are to be designated on a monitor.

As shown in FIG. 5, the fluorescent imaging device 61 of this embodiment is composed of an electronic endoscope 62, a light source 63, a CCU for white use 64, a fluorescent observation device 65, control center 66, and a monitor 67.

Unlike the endoscope 2 of FIG. 1, in electronic endoscope 62, the CCD for white use 68 is disposed at the imaging position of the object lens 32. Therefore, the electronic endoscope 62 does not have the image guide 33 and the eyepiece part 13. Also, CCD for white use 68 in this embodiment does not generate an image of reflected white light per se, but rather a synthesis of red, green and blue component color images within the visible region, as an equivalent of a white light image.

The signal conductor 68a connected to CCD for white use 68 passes from insertion part 11 through a light guide cable 14, and is connected to the CCU for white use 64 through an additional cable 64a which is connected to cable 68a through a suitable 64b.

Also, a forceps channel 71 is provided. A light tube 72 is positioned in forceps channel 71, as described in more detail below.

Light source device 63 includes a rotating filter 74 (FIG. 7) positioned on the optical path between rotary filter 23 and lamp 21. Rotary filter 74 is driven by a motor 75.

As shown in FIG. 6, the structure of filter 23 is the same as that in FIG. 2, and the output signal from photocoupler 28 is provided to a control circuit 77 within a control center 66.

As shown in FIG. 7, filter 74 comprises a red filter component 76 R, a green filter component 76 G, and a blue filter component 76 B as indicated by two-headed arrow 74a, filter 74 and the motor 75 are movably mounted so that filter 74 may be shifted out of the optical path of lamp 21. A suitable driver mechanism 78 operated by control circuit 74 is provided for this purpose.

Positioned within light tube 72 is an image guide 81. A lens 82 is located at the back end of image guide 81. A lens 82 is optically coupled to an imaging lens 83. A movable shutter 84 is disposed front of lens 83. Control center 66 includes a control circuit 77.

Among the functions of control circuit 77 are to operate movable shutter 84. In the position shown in FIG. 5 by solid lines, shutter 84 permits light to pass from lens 83 to the dichroic mirror 48. In the position indicated by the dotted lines, shutter 84 blocks light passing through lens 83 from reaching mirror 48. Mirror 48 is part of fluorescent imaging device 44 which is the same as that included in the first embodiment described in connection with FIG. 1.

The output signal of the CCDs 51 and 55 are provided to a common CCU for fluorescent use 85 within control center 66, which generates a fluorescent picture signal. This signal is coupled by switching arrangement 68 to a monitor 67. A picture signal from the CCU for white use 64 is also coupled by switching arrangement 68 to monitor 67.

A switch 87 is provided on the camera 73 to select the mode of operation. Based on the selection made by switch 87, circuit 77 controls the operation of shutter 84, driver 78 and switching arrangement 86 as described in more detail below. Control center 66 also provides operating power to camera 73 and CCU for white use 64.

In the second embodiment, essentially the same control functions are provided as in the first embodiment. For example, shutter 84 is normally in a closed condition. When a driving signal is provided by control circuit 77, the shutter is moved to an open condition. In addition, control circuit 77 monitors the ON/OFF condition of the power for light source 63. When the power source is turned ON, circuit 77 maintains shutter 84 in its closed condition during a start-up delay interval. When the power for light source 63 is turned OFF, circuit 77 immediately switches shutter 84 into its closed condition. Further description of the structural features is omitted in the interest of brevity.

The operational states for this embodiment are illustrated with reference to FIG. 8.

When the power sources for light source 63 and control center 66 are both OFF, the light source 63 does not generate a white light or an excitation light, and since the driving signal is not applied by control circuit 77 to shutter 84, shutter 84 remains in the "closed" position, as indicated in FIG. 8.

When the power source of the light source 63 is OFF but the power source for control center 66 is ON, at first, control circuit 77 keeps the shutter 84 in its closed condition. Therefore the shutter 84 is in the "closed" condition, as indicated in FIG. 8. Shutter 84 also remains closed during the start-up delay period when the power sources of both the light source 63 and control center 66 are turned on.

After the start-up delay period, if the white light imaging mode is selected by operation of switch 87, the control circuit 77 controls the rotation of the stepping motor 22 to position clear glass insert 25 on the optical path for lamp 21 and confirms the position by means of the detection signal of the photocoupler 28.

In response, the detection signal corresponding to the positioning of clear insert 25 in the path of lamp 21 shutter remains in the "closed" condition. Also, the control circuit 77 control the drive mechanism 78 to position the RGB rotary filter 74 on the optical path of lamp 21, and operates monitor 75 to rotate filter 74. As a result, recurring sequences of red, green, and blue light pulses pass through clear glass insert 25 of rotary filter 23 and are coupled to light guide 16 through lens 24. The light pulses are emitted onto the tissue under examination through the illumination lens 31. The light pulses which are reflected from the illuminated tissue are imaged onto the CCD for white use 68 by means of the object lens 32 as previously described in connection with the first embodiment.

The output signal from CCD for white use 68 undergoes signal conditioning at the CCU for white use 64 to convert it into a picture signal which is then displayed on the monitor 67 through switching arrangement 86.

When the fluorescent imaging mode is selected by means of switch 87, the control circuit 77 controls drive mechanism 78 to shift motor 75 and filter 74 out of the optical path of lamp 21, and operates stepping motor 22 to position blue filter 26 in the optical path. The proper positioning of blue filter 26 is confirmed by the detection signal from photocoupler 28, as previously described. When the control circuit 77 receives the detection signal indicating the blue filter 26 is properly positioned, it drives shutter 84 to the "open," position, as indicated in FIG. 8.

With filter 26 in place, only light with the blue wavelength is supplied into the light guide 16, to provide the excitation light for illuminating the tissue under examination.

The fluorescence generated by the excitation light is imaged at the tip plane of the image guide 81 by the lens 82, and is transferred through the image guide 81, to dichroic mirror 48 within the camera 73. As the light which is transmitted by dichroic mirror 48 passes through green filter 49 and then, after the light-amplification by the I.I. 50, is imaged with the CCD for fluorescent use 51.

On the other hand, the light which is reflected by the dichroic mirror 48 is further reflected by mirror 52, and passes through red filter 53. After light-amplification by I.I. 54, the red light is imaged at the CCD for fluorescent use 55.

The output signals of the CCDs for fluorescent use 51 and 55 undergo signal conditioning at the CCU for fluorescent use 85 and are converted into picture signals for display as fluorescent images on the monitor 67 under control of switching arrangement 86.

If the operating mode is switched from fluorescent to white light imaging, control circuit 77 first closes shutter 84, operates drive mechanism 78 to shift the RGB rotary filter 74 into operating position in front of lamp 21, and operates monitor 22 to set the clear glass insert 25 of the rotary filter 23 in the optical path of lamp 21.

Then, the RGB rotary filter 74 which is rotated by the motor 75, images the white light image as described above and the white light image is displayed on monitor 67.

Thus, according to this embodiment, before an operation mode is set, for example, during start-up, shutter 84 remains in its closed condition to prevent excessive light from being admitted to the fluorescent imaging device 44, with a consequent damage to the I.I.s 50 and 54.

When switching from fluorescent to white light imaging, shutter 84 is set to be closed before light source 63 is switched from emitting excitation light to emitting of white light. Similarly, when switching from white light to fluorescent imaging, shutter 84 is opened only after light source 63 is switched from emitting of white light to emitting of excitation blue light, again preventing admittance of an excessive light into the fluorescent imaging device 44.

A third embodiment of the present invention is illustrated in FIGS. 9 and 10.

As shown in FIG. 9, the rotary filter 23a differs from the rotary filter 23 of the first and second embodiments, in that an emergency light 91 is also provided.

As shown in FIG. 10, light source 63a is provided with rotary filter 23a and a burnt lamp detector 92. The latter detects if lamp 21 becomes inoperable, e.g., if it burns out, by monitoring the lamp output.

The detection signal from burnt lamp detector 92 is coupled to a control circuit 77 by a conductor 92a. If the light output of lamp 21 falls below a predetermined level as indicated by the signal on conductor 92a, control circuit 77 operates to active emergency light 91. Also, a warning device 93 is activated to warn an operator that the lamp 21 is inoperative.

In particular, if lamp 21 becomes inoperative during use, the burnt lamp detector signals control circuit 77 and warning device 93, which emits a signal by means of a buzzer, warning light or the like.

If this happens with the system in the fluorescent mode, control circuit 77 responds to the detection signal on conductor 92a to close shutter 84 (see FIG. 10) so that light transmitted through imaging lens 83 does not impinge on dichroic mirror 48.

Next, the control circuit 77 drives motor 22 to rotate the rotary filter 23a so that the light from the emergency light 91 is introduced into light guide 16. Then, once emergency light 91 is aligned with the light admittance end of light guide 16, control circuit 77 turns on emergency light 91 to secure a field of view.

Emergency light 91 may be activated before or at the same time as motor 22, as long as it is after shutter 84 has been closed. Alternatively, instead of closing shutter 84, the sensitivities of the I.I.s 50 and 54 may be reduced.

On the other hand, if white light is being used, when lamp 21 becomes inoperative, the control circuit 77 responds to the detection signal on conductor 92a to maintain shutter 84 in the closed position, and drives motor 22 to move rotary filter 23a into a position such that light from the emergency light 91 may be coupled into light guide 16. Then, when the rotation of filter 23a is completed, and emergency light 91 is positioned properly, control circuit 77 activates emergency light 91. Alternatively, emergency lamp 91 may be activated while motor 22 is still in motion.

Thus, in this third embodiment, whether lamp 21 becomes inoperative during the course of fluorescent observation or white light observation, the emergency light is not turned on until the image intensifiers have been protected.

In addition, since when the emergency light 91 is lighted, the blue filter 26 of the rotary filter 23a is always out of the optical path, sufficient illumination is provided for safe removal of endoscope 61.

Alternatively, in the third embodiment, provision may be for the operator to activate the emergency lighting sequence described above, for example, by means of a switch or the like.

Moreover, emergency light 91 may be, for example, a light emitting diode which emits a light with a wavelength within the detection band of the fluorescent imaging device. Therefore, if the lamp 21 becomes inoperative in the course of a fluorescent observation, the rotary filter 23a is rotated so that light from the light emitting diode is coupled to the light guide 16. On the other hand, if the lamp 2 becomes inoperative in the course of a white light observation, the shutter 84 which has been positioned to block the optical path of imaging lens 83 may be opened while the rotary filter 23a is being repositioned, after which light form the light emitting diode is coupled to the light guide 16.

In this way, imaging using the light emitting diode emergency light source may continue, and miniaturization, electric power-saving and reduction in costs of the illumination for emergency use can be achieved.

A fourth embodiment of the present invention which provides only fluorescent imaging is illustrated in FIGS. 11–14.

As shown in FIG. 11, the fluorescent imaging device 100 comprises a light source 101, an endoscope 102, an imaging subsystem or camera 103, an image processing subsystem 104, a monitor 105, and a color reference subsystem 106.

Light source 101 includes a lamp 101a which may be a metal halide lamp, a mercury lamp, or the like to provide a source of white light. A blue filter 101b is disposed in the optical paths of lamp 101a to generate an excitation light within the blue region, for example between about 400 nm and 450 nm.

Endoscope 102 has a slender insertion part 102a which is designed for insertion into the organism being examined, and an illumination system comprising a light guide 107a which transfers the excitation light from light source 101 to an illumination window 107b at the tip of insertion part 102a. Endoscope 102 also includes an observation optical system comprising an observation window 108a which couples a fluorescent image from the tissue under examination to an image guide 108b.

Image guide 108 terminates in an eyepiece section 102a. A lens 108c focuses the light output of light guide 108b for visual observation, or connection to camera 103.

Camera 103 is removably connected to eyepiece 102b. Camera 103 includes a dichroic mirror 110 which divides the fluorescent image from eyepiece lens 108c into a transmitted portion 110a and a reflected portion 110b. A first band pass filter 110 which transmits a wavelength band $\lambda_1$ is positioned to intercept transmitted light portion 110a from dichroic mirror 110. A second mirror 113 is positioned to intercept reflected light portion 110d and to reflect it in turn through a second band pass filter 112 having wavelength passband $\lambda_2$. A first image intensifier 114 amplifies the light transmitted by filter 111 and a second image intensifier 115 amplifies the light transmitted by filter 112. Image intensifiers 114 and 115 respectively provide outputs to CCD's 116 and 117.

Image processing circuit 104 and a color reference subsystem 106 provide visual data for display on monitor 105. Image processing circuit 104 converts the red and green image signals generated by CCD's 116 and 117 into a fluorescence image display signal. Color reference subsystem 106 includes a color reference generator 106a which generates a color discrimination scale display signal and a superimposing circuit 106b, which combines the fluorescence image display signal and the color discrimination scale display signal into a composite video signal for display on monitor 105. The display includes a portion 105a representing the tissue under examination and a color discrimination scale 105b. As explained below, color discrimination scale 105b provides a reference for objective identification of diseased tissues in accordance with color tone variations in the tissue image display 105a.

The operation of fluorescent imaging device 100 will now be illustrated.

The excitation light $\lambda_0$ within the blue region is generated by lamp 101a of the light source 101 and is then introduced into the light guide 107a of the endoscope 102. The excitation light $\lambda_0$ passes through light guide 107a and then is emitted through illumination window 107b toward the tissue under observation. The fluorescent image stimulated by the excitation light is transferred through the observation window 108a and the image guide 108b to the eyepiece part 102b at the operator side and then is emitted into the camera 103.

The fluorescent image which is emitted into the camera 103 is partially transmitted and partially reflected by dichroic mirror 110. The transmitted portion 111a passes through first bandpass filter 111; and after being amplified at the first image intensifier 114, is imaged at CCD 116 to undergo photoelectric conversion to an electric signal.

The reflected portion 110b of the fluorescent image is again reflected by the mirror 113 and then passes through second bandpass filter 112, and after being amplified at the second image intensifier 115, is imaged at CCD 117 to undergo photoelectric conversion to an electric signal.

As will be understood, the electric signals produced by CCDs 116 and 117 represent single-color fluorescent light images with different color tones. These are connected into the image processing circuit 104a which arithmetically processes the two input signals to generate the fluorescence image display signal.

As shown in FIG. 12, the fluorescence within the visible region which is stimulated by the excitation light shows an intensity distribution in a longer wavelength band than that of the excitation light $\lambda_0$ which is emitted from the light source device 101. Normal tissue shows a strong fluorescent intensity within the range near to the green region $\lambda_1$, especially of 490 nm through 560 nm, while for abnormal tissue such as that of cancer or the like, the fluorescent intensity is relatively weaker in this band. On the hand, the fluorescent intensity of abnormal tissue the red region $\lambda_2$, especially within the range of about 620 nm through about 800 nm, though attenuated compared to the intensity of normal tissue, is attenuated to a much lesser degree relative to normal tissue than in the green band $\lambda_1$. Accordingly, it is possible to utilize the differences in relative intensity between normal and abnormal tissue in the red and green bands to discriminate between and normal and abnormal tissue.

Therefore, the fluorescences which exist near green region $\lambda_1$ and red region $\lambda_2$ may be converted by image processing circuit 104 into a single fluorescence image display signal from which the condition of tissue may be observed, by viewing the tissue image display 105a on the screen of monitor 105.

To make it easy to discriminate visibly between normal and abnormal tissue, an image of the green region $\lambda_1$ is displayed as a cyan video signal and an image of the red region $\lambda_2$ is displayed as a red video signal.

Then, as shown in FIG. 13, when the tissue image 105a is displayed on monitor 105 with cyan and red, normal tissues are visualized as cyan and cancer lesions as dark red. A dysplasia, which is a precancerous lesion, is visualized as a lighter red.

The value of the difference or the ratio of the $\lambda_1$ and $\lambda_2$ image signals may be obtained from image processing circuit 104 as the fluorescence image display signal, the color of which corresponds to the value of the difference or the ratio. Referring still to FIG. 11, a color reference generator 106a, which may be of any conventional or desired design, combines a signal representing a cyan color and a signal representing a red color in various ratios to generate the color indication signal data representing the colors for a color discrimination scale 105b on monitor 105.

In this embodiment, as shown in FIG. 14, the coloration discrimination scale 105b comprises four distinct bands 200a–200d, respectively providing cyan, white, bright red and dark red reference colors. Color discrimination scale 105b is displayed on the monitor 105 by superimposing circuit 106b along with the tissue image 105a.

Therefore, an operator can make an objective discrimination of subtle coloration differences in the tissue image display by comparing the coloration of image 105a with the color reference bands 200a–200d in color discrimination scale 105b, and then can diagnose abnormal conditions such as the existence of a lesion, the extent of the lesion, and the like is an objective manner. In other words, a common discrimination standard can be provided which is independent of differences between operators and also in facilities such as hospitals and the like.

Although two single colors are used in this embodiment to form the tissue image 105a, many single colors may be mixed. Also, the color discrimination scale 105b is not limited to four color reference bands. Therefore, by displaying the tissue image while increasing the number of color reference bands as well as the relative brightness of individual colors, changes in appearance of the image due to the brightness of the fluorescent image can be confirmed. Moreover, the color discrimination scale 105b may be moved by means of superimposing circuit 106b to position it adjacent to a particular portion of tissue image 105a (or may even overlie other parts of image 105a) which makes color comparisons easer and more reliable. This may be done in any conventional or desired manner, as by use of a scale positioner 205 such as mouse or other manual input device.

A fifth embodiment of the present invention is illustrated in FIGS. 15–17.

As shown in FIG. 15, a fluorescent imaging device 100a of this embodiment includes light source 101, an endoscope 102 and a camera 103 which are the same as the corresponding components of the fourth embodiment, and an image processing circuit 104 described in detail below.

Light source 101 includes, by way of example, a wideband lamp 101a and a blue filter 101b which passes only blue and ultraviolet light to light guide 107a in endoscope 102. An illumination window 107b directs the excitation light onto the tissue under observation.

A fluorescent image generated in response to the excitation light is transferred through an observation window 108a and an image guide 108b in endoscope 102 to an eyepiece 102b, and is then coupled to camera 103 through the eyepiece lens 108c.

Image processing circuit 104 comprises first and second CCU's 143 and 146, respectively coupled to the outputs of first and second CCD's 116 and 117 in camera 103. First and second analog to digital (A/D) converters 144 and 147 are respectively connected to the outputs of CCU's 143 and 146. These, in turn, provide input signals for respective lookup tables (LUT's) 145 and 148. LUT 145 corrects the output of A/D converter 144 in accordance with the response characteristics of I.I. 114 and CCD 116 in camera 103, and LUT 148 adjusts the output of A/D converter 147 to match the response characteristics of the second I.I. 115 and the second CCD 117 in camera 103 to the typical characteristics of human vision. A video processor 149 generates tissue image display signals from the corrected data generated by LUTs 145 and 148 for display on monitor 105.

Image processing circuit 104 computes the maximum values of the brightness levels of the raw color image signals 152 and 154 provided by CCD's 116 and 117 and adjusts these signals to produce an output video display on monitor 105 in which normal tissue is displayed in a predetermined reference color. This is accomplished by a computation circuit 141, a control circuit 142, and a color tone adjustment switch 150.

Computation circuit 141 computes the frequencies of the brightness levels (histograms) of the image signals from LUTS 145 and 148, and control circuit 142 obtains the peak ratios of the distributions of the histograms for the green and red signals obtained by computation circuit 141, and also adjusts and controls the amplification ratios of I.I.s 114 and 115 so that the peak ratios are at the frequencies corresponding to the color tones of normal tissues. Image processing circuit 104 further includes a color tone adjustment switch 150 which initiates the process of adjustment of the amplification ratio.

In operation, camera 103 functions as described in connection with the fourth embodiment to produce image signals on conductors 152 and 154 respectively representing the green and red components of the fluorescent image.

The green fluorescent image signal on conductor 152 is processed by the first CCU 143 and then is converted into a digital signal by A/D converter 144. Then this digital data is corrected to match the response characteristics of human vision by the first LUT 145 where the correction data which are fitted to the response characteristics of the first I.I. 114 and the first CCD 116 are recorded.

The red fluorescent image signal appearing on conductor 154 is processed by CCU 146 and then is converted into a digital signal by A/D converter 147. This digital data is corrected to match the response characteristics of human vision by the second LUT 148 where the correction data which are fitted to the response characteristic of the second I.I. 115 and the second CCD 117 are recorded.

The corrected digital signals are used to generate a so-called pseudo color image signal in video processor 149. This is displayed as an image representing the tissue under examination on the screen of the monitor 105. The color tone of the tissue image corresponds to the ratio of the digital data for the green and red fluorescent images produced by LUTs 145 and 148 respectively. In order words, for a normal tissue characterized by a green image component which is larger than the red component, the image is displayed with a cyan color tone, and in the case of an abnormal tissues such as cancer tissues where the red component is larger than green components, the image is displayed with a red color tone.

However, if the gain or amplification of the second I.I. 115 which amplifies the red fluorescence is relatively higher than the gain of first I.I. 114 which amplifies the green fluorescence, normal tissue will be displayed with a whitish cyan coloration and an abnormal tissue will be displayed with a much more reddish coloration. On the other hand, if the gain of second I.I. 115 is much lower than that of first I.I. 114, normal tissue will be displayed with a much greater cyanic color tone and abnormal tissue will be displayed with a darker color.

To calibrate the system so normal tissue is displayed in the desired cyan color, the operator pushes color tone adjustment switch 150 while observing normal tissue. This automatically starts the color tone adjustment process.

In general, the gain of the second I.I. 115 which amplifies the red fluorescence is related to the gain of I.I. 114 which amplifies the green fluorescence according to the relationship:

$$R(G) = aG^2 + bG + c \qquad (1)$$

Here, R is the gain of the second I.I. 115, G is the gain of the first I.I. 114. The coefficients (a) and (b) and additive term (c) are constants.

Coefficient (a) corrects for non-linearity of the individual gain characteristics of the I.I.s 114 and 115, and coefficient (b) corrects the relative gains of the I.I.s 114 and 115. Constant term (c) is an offset value.

By adjusting the value of (b), adjustment of the color tone for normal tissue can be achieved.

To simplify the illustration of the process of the color tone adjustment which is described hereinafter, the values of (a) and (c) are set to be 0, i.e. that there is no non-linearity or offset. Referring to FIGS. 16A, 16B and 17, to begin the process, color tone adjustment switch 150 is pushed as described above during the observation of normal tissues. At Step S1, computation circuit 141 operates control circuit 142 to set the gain of I.I.'s 114 and 115 to be equal, i.e., b=1 in equation (1). Using these gain values, the green and red fluorescent image signals 152 and 154 are processed by CCU's 143 and 146, A/D converters 144 and 147, and LUT's 145 and 148 as described above, and the resulting image signals provided by LUT's 145 and 148 are provided to computation circuit 141. The process then shifts to Step S2.

At Step S2, as shown in FIG. 16A and FIG. 16B, the histograms of the red and green image signals are calculated. The process then shifts to Step S3 where from the histogram of the individual colors, namely those of red and green, the maximum values for green $H_G$ and red $H_R$ are computed. The process then shifts to Step 4, where the ratio $R=(H_G/H_R)$ of the maximum value for green, $H_G$ and the maximum value for red, $H_R$ is obtained.

The process then shifts to Step S5 where the value of the ratio R which is obtained in Step S4 is compared with a first reference value $R_1$. If $R<R_1$ the process shifts to Step S6 where the value of the term b is increased by, for example 0.1 and the treatment from Step S2 is repeated again using LUT values for relative gain represented by b=1.1. Therefore, until $R>R_1$, the steps from Step S2 to Step S5 are repeatedly performed. When the value of the ratio R becomes larger than the $R_1$, the process shifts to Step S7.

Here, the value of R for which $R>R_1$ is compared to a second reference value $R_2$. If $R>R_2$, the process shifts to Step S8 where the value of the term b is reduced by, for example, 0.1, and steps S2–S5 and S7 are repeated.

The process continues as described until the value of R falls within the range $R_2>R>R_1$. When this condition is satisfied, the process terminates.

For the above-described computation process it is found that the values of $R_1$ and $R_2$ should be set to a relatively wide value compared to the changes in the value by 0.1 in Step S8.

As a result of the above-described enhancement process, normal tissues are displayed on monitor 105 in an easily recognized cyan color, and abnormal tissues are displayed in an equally recognizable dark red color tone. As a result, an operator can objectively discriminate between normal and abnormal tissues and easily identify lesions, cancerous and precancerous tissues, etc.

FIG. 18 illustrates a sixth embodiment of the present invention which in effect combines the features of the first and fourth embodiments. For this embodiment, camera 4 (not shown) which is identical to that shown in FIG. 1, provides a white image output signal from CCD 40 and fluorescent image output signals from CCDs 51 and 55. These are provided as inputs to control center 5'. This includes CCU for white use 41 which receives as its input the white image signal from CCD 40, and image processing circuit 104a which receives its inputs from CCDs 51 and 55 (see FIG. 11). CCU for white use 41 provides an input to switching arrangement 42, a second input to which is provided by superimposing circuit 106b. This in turn receives its inputs from image processing circuit 104a, color reference generator 106a and positioning device 205, all of which function in the manner of the correspondingly numbered elements described in connection with FIG. 11.

Control center 5' also includes a control circuit 8 and a start switch 7. Control circuit 8 provides a control output to switching arrangement 42 to select whether the white light image provided by CCU for white use 41 or the fluorescent image provided by superimposing circuit 106b is coupled to a monitor 6. Control circuit 8 receives additional inputs and provides additional outputs as described in connection with FIG. 1.

FIG. 19 shows a seventh embodiment of the present invention which essentially combines the features of the first and the fifth embodiments. Here, camera 4 (not shown) and monitor 6 function essentially in the same manner as described in connection with FIG. 1, and control center 5" performs a combination of the functions of control center 5 of FIG. 1 and image processing circuit 104 of FIG. 15.

Specifically, control center 5" includes CCU for white use 41 which processes the white light image signal provided by CCD 40, CCU 143, A/D converter 144, and Look Up Table (LUT) 145 which process the green color band component signal of the fluorescent image, and CCU 146, a/d converter 147 and LUT 148 which process the red color component signal of the fluorescent image. The outputs of LUTS 145 and 148 are coupled to video processor 149. All of these elements function in the same manner as the correspondingly numbered elements described in connection with FIG. 15. Video processor 149 provides a second signal input to switching arrangement 42. A control signal input for switching arrangement 42 is provided by control circuit 8 which selects between the white light video signal and the fluorescent light video signal in the manner described in connection with FIG. 1.

Control center 5" also includes computation circuit 141, image intensifier control circuit 142 and calibration start switch 150 all of which function in the manner described with respect to the like numbered elements in FIG. 15.

As previously indicated, the sixth and seventh embodiments respectively illustrated in FIGS. 18 and 19 function in the same manner as the embodiment of FIG. 1 to select between display of a white light image or a fluorescent image and to protect the high sensitivity imaging circuits used to process the fluorescent image color band data. The sixth embodiment operates as described in connection with FIGS. 11 through 14 to provide an enhanced fluorescent image display and a color reference display for simultaneous presentation on the monitor, while the seventh embodiment operates in the manner described in connection with FIGS. 15 through 17 to provide color and light level correction for the video display of the fluorescent image.

Although the present invention has been described in relation to particular embodiments thereof, many other variations and modifications and other uses will be apparent to those skilled in the art. It is intended, therefore, that the present invention be limited not by the specific disclosure herein, but only by the appended claims.

What is claimed is:

1. A fluorescent imaging system for use with an endoscope including a first light guide for illuminating tissue under examination and a second light guide for transmitting tissue image data resulting from such illumination, the imaging system comprising:

a light source for connection to the first light guide which generates excitation light at a frequency which will excite a fluorescent response from the tissue under examination;

a fluorescent imaging device for connection to the second light guide and responsive to image data provided thereby, the imaging device including:

an optical system which separates the image data into at least two color bands, and electro-optical circuitry that generates electrical signals representative of the optical image data for each color band;

an image processing subsystem coupled to the imaging device including:

a conversion circuit operative to convert the electrical signals representative of the optical image data for each color band respectively into predetermined color image signals; and a video signal generating circuit responsive to the color image signals to generate a first video signal which represents an enhanced image of fluorescence in the tissue under examination; and a display device for displaying the fluorescence image;

an interpretation reference subsystem that generates a second video signal representing a tissue fluorescence image color interpretation guide related to the predetermined color image signals for display on the display device; and a superimposing circuit that combines the first and second video signals to display the fluorescence image and the interpretation guide together on the display device.

2. A fluorescent imaging system according to claim 1, wherein:

the imaging device generates a first electrical signal representative of optical image data in a color band within a first portion of the spectrum, and a second electrical signal representative of optical image data in a color band within a second portion of the spectrum, and wherein the image processing subsystem generates the first video signal as a function of the ratio of the first and second electrical signals.

3. A fluorescent imaging system according to claim 1, wherein:

the imaging subsystem generates a first electrical signal representative of optical image data in a color band within a first portion of the spectrum, and a second electrical signal representative of optical image data in a color band within a second portion of the spectrum, and wherein the image processing subsystem generates the first video signal as a function of the difference between the first and second electrical signals.

4. A fluorescent imaging system according to claim 1, wherein the optical system comprises:

a beam splitter which provides a plurality of light beams; and a plurality of optical filters, one filter being positioned in the path of each of the light beams and respectively corresponding to one of the color bands.

5. A fluorescent imaging system according to claim 4, wherein the beam splitter comprises at least one dichroic mirror.

6. A fluorescent imaging system according to claim 5, wherein the electro-optical circuitry comprises:

an imaging intensifier optically coupled to each of the filters, and a charge coupled device optically coupled to the output of each of the image intensifiers.

7. A fluorescent imaging system according to claim 1, wherein the electro-optical circuitry comprises:

a light amplifier in the path of each of the color bands; and an opto-electric converter optically coupled to the output of each of the light amplifiers.

8. A fluorescent imaging system according to claim 7, where each of the light amplifiers is an image intensifier.

9. A fluorescent imaging system according to claim 7, wherein each of the opto-electric converters is a charge coupled device.

10. A fluorescent imaging system according to claim 1, wherein the image processing subsystem comprises:

an image processing circuit responsive to the image data electrical signals, and which generates a color separation video signal for each of the color bands; and a video processor which combines the color separation video signals to generate the first video signal.

11. A fluorescent imaging system according to claim 10, wherein:

the electro-optical circuitry in the imaging device includes a plurality of light amplification devices, one of the light amplification devices being provided for each of the image data color bands; and wherein the image processing subsystem further comprises:

a computation circuit responsive to the color separation video signals to determine the relative amplification of each of the light amplification devices; and a control circuit connected to the computation circuit, the control circuit and the computation circuit being operative together to adjust the relative amplification of the light amplification devices in accordance with a predetermined computational routine.

12. A fluorescent imaging system according to claim 11, wherein the control circuit is responsive to an external command to initiate the predetermined computational routine; and wherein the predetermined computational routine sets the relative amplification to a predetermined initial value, and then recursively determines the ratio of the maximum values of the color separation video signals, compares the ratio with upper and lower reference values, adjusts the relative amplification upward by a predetermined amount if the ratio is less than the lower reference value, and adjusts the relative amplification downward by the predetermined amount if the ratio is greater than the upper reference value, and again determines the ratio of the maximum values of the color separation video signals, the routine being repeated until the ratio falls between the upper and lower reference values.

13. A fluorescent imaging system as described in claim 1, in which the interpretation reference subsystem generates a color discrimination scale as the second video signal, and in which the superimposing circuit combines the first and second video signals to display the fluorescence image and the color discrimination scale as the fluorescence image interpretation reference together on the display device.

14. A fluorescent imaging system according to claim 13, further including:

a manual input device for positioning the color discrimination scale at any desired location relative to the tissue fluorescence image on the display device.

15. A fluorescent imaging system according to claim 1, further including:

a manual input device for positioning the image interpretation guide at any desired location relative to the tissue fluorescence image on the display device.

16. A fluorescent imaging system according to claim 1, wherein the interpretation reference subsystem comprises:

a color reference generator that generates a plurality of color reference signals, each representing one of the image data color bands; and a video circuit responsive to the color reference signals to generate a color discrimination scale as the second video signal.

17. A fluorescent imaging system according to claim 16, wherein the color discrimination scale is in the form of the plurality of stacked color bars, each bar corresponding to one of the colors represented by the color discrimination signals.

18. A fluorescent imaging system according to claim 17, wherein the colors represented by the color discrimination signals are cyan, white, bright red and dark red.

19. A fluorescent imaging system according to claim 17, further comprising:

a manual input device for positioning the color discrimination scale at any desired location relative to the tissue fluorescence image on the display device.

20. A fluorescent imaging system according to claim 16, wherein the second circuit includes:

a separate circuit path for each of the different colors, each circuit path including a plurality of variable gain devices, one of which is connected to a different one of the reference signal sources; and a combining circuit connected to the output of each of the variable gain circuits to generate one of the color discrimination signals, the gain of each of the variable gain circuits being adjusted so that the output of the combining circuit represents the desired color.

21. A fluorescent imaging system according to claim 20, wherein:

the reference signals represent a red color band, and a green color band; and wherein the color discrimination signals represent cyan, white, bright red and dark red color bars in the color discrimination scale.

22. A fluorescent imaging system according to claim 1, in which the light source is selectively operable to generate white light and excitation light; and further including:

a further imaging device coupled to the second light guide including a first electro-optical subsystem which generates an electrical signal representing a white-light image of the tissue under examination resulting from exposure to white light;

a further image processing subsystem coupled to the further imaging device that converts the white light image electrical signal into a white-light video signal; and a switching device which selectively connects the first or the second video signal to the display device.

23. A fluorescent imaging system according to claim 22, further including a protective device that prevents damage to the fluorescent imaging device due to impingement of a white-light image thereon.

24. A fluorescent imaging system according to claim 23, wherein the protective device is operative to prevent impingement of a white light image on the fluorescent imaging device.

25. A fluorescent imaging system according to claim 23, wherein the protective device is operative to reduce the sensitivity of the fluorescent imaging device when excitation light is not being generated.

26. A fluorescent imaging system according to claim 23, further including an optical path switching device which blocks the passage of light to the fluorescent imaging device when the light source is not emitting excitation light.

27. A fluorescent imaging system according to claim 23, wherein the protective device prevents the light source from generating white light when the fluorescent imaging device is activated.

28. A fluorescent imaging system according to claim 23, wherein the protective device is operative to shut down the fluorescent imaging device when excitation light is not being generated.

29. A fluorescent imaging system according to claim 22, in which the interpretation reference subsystem generates a color discrimination scale as the second video signal, and in which the superimposing circuit combines the first and second video signals to display the fluorescence image and the color discrimination scale as the fluorescence image interpretation reference together on the display device.

30. A fluorescent imaging system according to claim 29, further including a manual input device connected to the superimposing circuit which is operative to position the color discrimination scale at any desired location relative to the tissue fluorescence image on the display device.

31. A fluorescent imaging system according to claim 29, wherein the color discrimination scale is in the form of a plurality of stacked bars, each bar being of a different color.

32. A fluorescent imaging system according to claim 23, wherein the light source is comprised of:
   a first illumination device for selectively generating the white light or the excitation light;
   a second illumination device;
   a light detector coupled to a first illumination device;
   a switching device for selectively activating the first or the second illumination device; and
   a control circuit for the switching device responsive to the output of the light detector to deactivate the first illumination device and to activate the second illumination device when abnormalities are detected in the light output of the first illumination device.

33. An imaging system according to claim 32, wherein the second illumination device is a light emitting diode which emits light at the wave length of the excitation light.

34. A fluorescent imaging method for identifying abnormal tissue the method comprising the steps of:
   illuminating the tissue under examination with excitation light at a frequency which will excite a fluorescent response;
   collecting optical image data representing the fluorescent response;
   separating the collected optical image data into at least two color bands;
   generating electrical signals representative of the optical image data for each color band;
   converting the electrical signals representative of the optical image data for each color band into predetermined color image signals;
   forming a first video signal from the predetermined color image signals which represents an enhanced image of fluorescence excited in the tissue under examination;
   displaying the first video signal on a display device;
   generating a visual tissue fluorescence image color interpretation guide related to the predetermined color image signals; and
   displaying the fluorescence image and the fluorescence image interpretation guide together on the display device.

35. A fluorescent imaging method as described in claim 34, in which the color interpretation guide is a color discrimination scale in the form of a plurality of stacked color bars, each bar being of a predetermined color.

36. A fluorescent imaging method according to claim 35, wherein the step of generating the color discrimination scale comprises:
   generating a plurality of reference signals, each signal representing one of the color bands;
   generating a plurality of color bar signals, each signal representing one of the color bars, from the reference signals; and
   generating a second video display signal from the plurality of color bar signals which represents an image of the plurality of stacked color bars.

37. A fluorescent imaging method according to claim 36, wherein each of the color bar signals is generated by combining the reference signals after adjusting the amplitudes thereof to values which will yield a video display of the required color.

38. A fluorescent imaging method according to claim 35, wherein the step of generating the color discrimination scale comprises:
   generating a first reference signal which represents a red color band;
   generating a second reference signal which represents a green color band;
   generating cyan, white, bright red and dark red color bar signals, from the reference signals; and
   generating a second video display signal from the cyan, white, bright red and dark red color bar signals.

39. A fluorescent imaging method according to claim 35, further comprising the step of moving the color discrimination scale to a location on the display device in close proximity to a selected portion of the tissue fluorescence image display.

40. A fluorescent imaging method according to claim 35, further comprising the step increasing the number of color bars in the color discrimination scale on the display device while displaying tissue fluorescence image.

41. A fluorescent imaging method according to claim 34, further comprising the step of moving the image interpretation reference to a location on the display device in close proximity to a selected portion of the tissue fluorescence image display.

42. A fluorescent imaging method according to claim 34, in which the image interpretation reference is in the form of a color discrimination scale; and further including the step of displaying the enhanced fluorescence image and the color discrimination scale together on the display device.

43. A fluorescent imaging method according to claim 42, wherein the step of generating the image interpretation reference comprises:
   generating a plurality of reference signals, each signal representing each of the color bands;
   generating a plurality of color discrimination signals, each signal representing a predetermined index color, from the reference signals; and
   generating a second video display signal from the plurality of color discrimination signals which represents an image of the plurality of index colors displayed adjacent to each other.

44. A fluorescent imaging method according to claim 43, wherein each of the color discrimination signals is generated by combining the reference signals after adjusting the amplitudes thereof to values which will yield a video display of the required index color.

45. A fluorescent imaging method according to claim 44, wherein the index colors are cyan, white, bright red and dark red.

46. An imaging method according to claim 42, wherein the step of preventing damage to the opto-electric devices comprises preventing impingement of white light thereon.

47. A fluorescent imaging method according to claim 42, wherein the step of preventing damage to the opto-electric devices comprises reducing the sensitivity thereof when excitation light is not being generated.

48. An imaging method according to claim 42, wherein a primary illumination source selectively provides white light or excitation light and a secondary illumination source provides only excitation light, and wherein the step of preventing damage to the opto-electric devices comprises deactivating the primary illumination source in case of abnormalities in the light output thereof, and thereafter activating the secondary illumination source, and maintaining the opto-electrical devices in a disabled condition until the secondary illumination source is activated.

49. A fluorescent imaging method according to claim 34, further including:
   selectively illuminating the tissue under examination with white light or excitation light;
   creating an image of the tissue under examination resulting from exposure to the white light;
   generating an electrical signal representing a white light image;
   processing the white light image electrical signal to generate a second video signal;
   selectively displaying the first or the second video signal on a display device; and
   preventing damage to the opto-electric devices which generate the fluorescence image electrical signals due to impingement of a white light image thereon.

50. A fluorescent imaging method according to claim 49, further including the steps of generating a third video signal for displaying a color discrimination scale on the display device, and superimposing the second and third video signals for simultaneous display on the display device.

51. A fluorescent imaging method according to claim 50, further comprising the step of manually adjusting the third video signal to position the color discrimination scale at a desired location relative to the tissue fluorescence image on the display device.

52. A fluorescent imaging method according to claim 50, wherein the color discrimination scale is displayed in the form of a plurality of stacked color bars, each bar being of a different color.

53. A fluorescent imaging system according to claim 52, wherein the color bars are cyan, white, bright red and dark red.

54. A fluorescent imaging method according to claim 50, further including the step of increasing the number of colors in the color bar display while displaying the fluorescent image on the display device.

55. A fluorescent imaging method according to claim 49, wherein the step of generating the second video signal comprises combining the fluorescent image electrical signals as a function of the ratio of the first and second image data signals.

56. A fluorescent imaging method according to claim 49, wherein the step of generating the fluorescent image electrical signals comprises:
   generating a first image signal representative of image data in a color band within a first portion of the spectrum; and
   generating a second image signal representative of image data in a color band within a second portion of the spectrum, and wherein
   the step of generating the second video signal comprises generating a signal as a function of the difference between the first and second image data signals.

57. A fluorescent imaging method according to claim 49, wherein the step of separating the fluorescent image into color bands comprises:
   splitting the optical image data a plurality of light beams; and
   filtering each of the light beams with a filter corresponding to one of the color bands.

58. A fluorescent imaging method according to claim 57, wherein the step of generating the image data electrical signals further comprises:
   amplifying each of the optical image data color bands; and
   converting each of the amplified color bands into an electrical signal.

59. A fluorescent imaging method according to claim 49, wherein:
   the image data electrical signals are generated by separate electro-optical devices which convert the optical image for each color band into electrical signals; and wherein
   the step of forming the second video signal further comprises:
   separately enhancing the electro-optically generated signals for each color band in accordance with predetermined characteristics of the separate electro-optical devices; and
   combining the separately enhanced electrical signals.

60. A fluorescent imaging method according to claim 49, wherein:
   the step of generating the fluorescent image electrical signals further comprises separately amplifying the optical image data for each color band; and thereafter converting the amplified optical image data to an electrical signal.

61. A fluorescent imaging method according to claim 60, wherein:
   the step of generating the first video signal further comprises:
   adjusting the relative amplification of the optical image data in accordance with a predetermined computational routine.

62. A fluorescent imaging method according to claim 34, wherein the step of generating the image data electrical signals comprises:
   generating a first image data signal representative of image data in a color band within a first portion of the spectrum; and
   generating a second image data signal representative of image data in a color band within a second portion of the spectrum, and wherein
   the step of combining the separate image data signals comprises generating a signal as a function of the ratio of the first and second image data signals.

63. A fluorescent imaging method according to claim 34, wherein the step of generating the image data electrical signals comprises:
  generating a first image data signal representative of image data in a color band within a first portion of the spectrum; and
  generating a second image data signal representative of image data in a color band within a second portion of the spectrum, and wherein
  the step of combining the separate image data signals comprises generating a signal as a function of the difference between the first and second image data signals.

64. A fluorescent imaging method according to claim 34, wherein the step of separating the collected optical image data into color bands comprises:
  splitting the optical image data a plurality of light beams; and
  filtering each of the light beams with a filter corresponding to one of the color bands.

65. A fluorescent imaging method according to claim 64, wherein the step of generating the image data electrical signals comprises:
  amplifying each of the optical image data color bands; and
  converting each of the amplified color bands into an electrical signal.

66. A fluorescent imaging method according to claim 34, wherein:
  the image data electrical signals are generated by separate electro-optical devices which convert the optical image data for each color band into electrical signals; and wherein
  the step of forming the first video signal comprises:
  separately enhancing the electro-optically generated signals for each color band in accordance with predetermined characteristics of the separate electro-optical devices; and
  combining the separately enhanced electrical signals.

67. A fluorescent imaging method according to claim 66, wherein:
  the step of generating the image data electrical signals further comprises separately amplifying the optical image data for each color band; and thereafter converting the amplified optical image data to an electrical signal.

68. A fluorescent imaging method according to claim 67, wherein the step of generating the first video signal further comprises adjusting the relative amplification of the optical image data in accordance with a predetermined computational routine.

69. A fluorescent imaging method according to claim 68, further including the step of initiating the predetermined computational routine with an external command; and wherein the predetermined computational routine comprises:
  setting the relative amplification to a predetermined initial value, and then recursively
  determining the ratio of the maximum values of the color separation video signals,
  comparing the ratio with upper and lower reference values,
  adjusting the relative amplification upward by a predetermined amount if the ratio is less than the lower reference value,
  adjusting the relative amplification downward by the predetermined amount if the ratio is greater than the upper reference value, and
  again determining the ratio of the maximum values of the color separation video signals, the routine being repeated until the ratio falls between the upper and lower reference values.

* * * * *